(12) United States Patent
Wang et al.

(10) Patent No.: US 12,161,874 B2
(45) Date of Patent: Dec. 10, 2024

(54) IMPLANTABLE, BIOFUEL CELLS FOR SELF-CHARGING MEDICAL DEVICES

(71) Applicant: The Regents of the University of California, Oakland, CA (US)

(72) Inventors: Joseph Wang, San Diego, CA (US); Krishnan Chakravarthy, San Diego, CA (US); Itthipon Jeerapan, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 558 days.

(21) Appl. No.: 17/293,897

(22) PCT Filed: Nov. 14, 2019

(86) PCT No.: PCT/US2019/061537
§ 371 (c)(1),
(2) Date: May 13, 2021

(87) PCT Pub. No.: WO2020/102580
PCT Pub. Date: May 22, 2020

(65) Prior Publication Data
US 2022/0008737 A1    Jan. 13, 2022

Related U.S. Application Data

(60) Provisional application No. 62/767,389, filed on Nov. 14, 2018.

(51) Int. Cl.
*H01M 4/86* (2006.01)
*A61N 1/36* (2006.01)
(Continued)

(52) U.S. Cl.
CPC ....... *A61N 1/3785* (2013.01); *A61N 1/36062* (2017.08); *H01M 4/8673* (2013.01);
(Continued)

(58) Field of Classification Search
CPC .... H01M 8/004; H01M 8/16; H01M 2220/30; H01M 4/926; H01M 8/1018; A61N 1/3785; A61N 1/36062
See application file for complete search history.

(56) References Cited

U.S. PATENT DOCUMENTS

| | | |
|---|---|---|
| 6,862,479 B1 | 3/2005 | Whitehurst et al. |
| 7,368,190 B2 | 5/2008 | Heller et al. |
| (Continued) | | |

FOREIGN PATENT DOCUMENTS

| | | |
|---|---|---|
| WO | 2008035258 A2 | 3/2008 |
| WO | 2011117357 A2 | 9/2011 |

OTHER PUBLICATIONS

Arshak, K. et al., "Conducting polymers and their applications to biosensors: Emphasizing on foodborne pathogen detection", IEEE Sens. J. 2009, 9, 1942-1951.

(Continued)

*Primary Examiner* — Stewart A Fraser
(74) *Attorney, Agent, or Firm* — Perkins Coie LLP

(57) ABSTRACT

Disclosed are devices, systems and methods for implantable a biofuel cells. In some aspects, a biofuel cell device for extracting energy from a biological fluid includes a substrate including two compartments each with one or more openings; an anode assembly disposed in the substrate and including an anode electrode and functionalization material to facilitate an oxidative process that releases electrons captured at the anode electrode; and a cathode assembly disposed in the substrate separated from the anode assembly and including a catalytic material facilitate a chemical reduction process such that the biofuel cell device extracts electrical energy from the substance in the biological fluid.

21 Claims, 23 Drawing Sheets

(51) Int. Cl.
*A61N 1/378* (2006.01)
*H01M 8/00* (2016.01)
*H01M 8/16* (2006.01)

(52) U.S. Cl.
CPC ............ *H01M 8/004* (2013.01); *H01M 8/16* (2013.01); *H01M 2220/30* (2013.01)

(56) References Cited

U.S. PATENT DOCUMENTS

| | | | |
|---|---|---|---|
| 2005/0118494 | A1 | 6/2005 | Choi |
| 2005/0255345 | A1 | 11/2005 | Gerritse et al. |
| 2005/0260492 | A1 | 11/2005 | Tucholski et al. |
| 2006/0063043 | A1 | 3/2006 | Zeikus et al. |
| 2008/0044721 | A1 | 2/2008 | Heller et al. |
| 2008/0160384 | A1 | 7/2008 | Iqbal et al. |
| 2009/0305089 | A1 | 12/2009 | Minteer et al. |
| 2010/0099010 | A1 | 4/2010 | Niessen et al. |
| 2011/0135966 | A1 | 6/2011 | Jayaprakash |
| 2011/0143225 | A1 | 6/2011 | Nakagawa et al. |
| 2011/0250510 | A1 | 10/2011 | Cinquin et al. |
| 2011/0274959 | A1 | 11/2011 | Bailey et al. |
| 2012/0035434 | A1* | 2/2012 | Ferren ............... A61B 5/4839 600/301 |
| 2014/0024102 | A1* | 1/2014 | Sakai ............... C12N 9/0006 435/252.33 |
| 2014/0322617 | A1* | 10/2014 | Wang ............... H01M 4/8807 427/553 |

OTHER PUBLICATIONS

Barton, S. C. et al., "Enzymatic biofuel cells for implantable and microscale devices", Chem. Rev. 2004, 104, 4867-4886.
Bedekar, A.S. et al., "Oxygen limitation in microfluidic biofuel cells", Chem. Eng. Commun. 2007, 195, 256-266.
Davis, F. et al., "Biofuel cells—recent advances and applications", Biosens. Bioelectron. 2007, 22, 1224-1235.
Gerard, M. et al., "Application of conducting polymers to biosensors", Biosens. Bioelectron. 2002, 17, 345-359.
Goldberg, H. D. et al., "Screen printing: A technology for the batch fabrication of integrated chemical-sensor arrays", Sens. Actuat. B 1994, 21, 171-183.
ISA, International Search Report and Written Opinion for PCT Application No. PCT/US2019/061537. Mail Date: Jan. 29, 2020. 14 pages.
ISA, International Search Report, International Application No. PCT/US2012/067481, Nov. 8, 2013, 12 pages.
Kadara, R. O. et al., "Characterization and fabrication of disposable screen printed microelectrodes", Electrochem. Commun. 2009, 11, 1377-1380.
Kim, J. et al., "Challenges in biocatalysis for enzyme-based biofuel cells", Biotechnol. Adv. 2006, 24, 296-308.
Metters, J.P. et al., "New directions in screen printed electroanalytical sensors: An overview of recent developments", Analyst 2011, 136, 1067-1076.
Moehlenbrock, M. J. et al., "Extended lifetime biofuel cells", Chem. Soc. Rev. 2008, 37, 1188-1196.
Parashkov, R. et al., "Large area electronics using printing methods", Proc. IEEE 2005, 93, 1321-1329.
Ramanavicius, A. et al., "Enzymatic biofuel cell based on anode and cathode powered by ethanol", Biosens. Bioelectron. 2008, 24, 761-766.
Rogers, J. A. et al., "Printing process suitable for reel-to-reel production of high-performance organic transistors and circuits", Adv. Mater. 1999, 11, 741-745.
Sattayasamitsathit, S. et al., "Highly dispersed Pt nanoparticle-modified 3D porous carbon: A metallized carbon electrode material", Electrochem. Commun. 2011, 13, 856-860.
Smolander, M. et al., "Development of a printable laccase-based biocathode for fuel cell applications", Enzyme Microb. Tech., 2008, 43, 93-102.
Tudorache, M. et al., "Biosensors based on screen-printing technology, and their applications in environmental and food analysis", Anal. Bioanal. Chem. 2007, 388, 565-578.
Wang, J. "Electrochemical glucose biosensors", Chem. Rev. 2008, 108, 814-825.
Yang, X. Y. et al., "Immobilization technology: A sustainable solution for biofuel cell design", Energy Environ. Sci. 2012, 5, 5540-5563.
Yu, E. H. et al., "Enzymatic biofuel cells—fabrication of enzyme electrodes", Energies 2010, 3, 23-42.
Zhou, M. et al., "A self-powered 'Sense-Act-Treat' system that is based on a biofuel cell and controlled by Boolean logic", Angew. Chem. Int. Ed. 2012, 51, 2686-2689.
Zhou, M. et al., "Biofuel cells for self-powered electrochemical biosensing and logic biosensing: A review", Electroanal. 2012, 24, 197-209.
Zhou, M. et al., "DNAzyme logic-controlled biofuel cells for self-powered biosensors", Chem. Commun. 2012, 48, 3815-3817.
Andoralov, V., et al. (2013). "Biofuel Cell Based on Microscale Nanostructured Electrodes with Inductive Coupling to Rat Brain Neurons" *Sci. Rep.* 3: 3270. 11 pages.
Bonizzato, M., et al. (2018). "Brain-controlled modulation of spinal circuits improves recovery from spinal cord injury" Nat. Commun. 9(1): 3015. 14 pages.
Borgens, R.B., et al. (1981). "Enhanced spinal cord regeneration in lamprey by applied electric fields" Science, 213(4508), pp. 611-617.
Bradley, K. (2006). "The Technology: The Anatomy of a Spinal Cord and Nerve Root Stimulator: The Lead and the Power Source." Pain Medicine 7(suppl_1): S27-S34.
Capogrosso, M., et al. (2016). "A brain-spine interface alleviating gait deficits after spinal cord injury in primates." Nature 539. 23 pages.
Grattieri, M., et al. (2016). "Facilitated Electron Hopping in Nanolayer Oxygen-Insensitive Glucose Biosensor for Application in a Complex Matrix." ChemElectroChem 3(11): 1884-1889.
Herdman, K. M., et al. (2019). "Evaluating the ability of energy dispersive X-ray analysis to monitor binding oil content of carbon paste electrodes exposed to biofouling agents." J. Electroanal. Chem. 847: 113237. 9 pages.
Holsheimer, J. (1998) "Computer modelling of spinal cord stimulation and its contribution to therapeutic efficacy" Spinal cord, 36(8), p. 531-540.
Jeerapan, I., et al. (2018). "Enzymatic glucose/oxygen biofuel cells: Use of oxygen-rich cathodes for operation under severe oxygen-deficit conditions." Biosens. Bioelectron. 122: 284-289.
Kavanagh, P. et al. (2013). "Mediated electron transfer in glucose oxidising enzyme electrodes for application to biofuel cells: recent progress and perspectives." Phys. Chem. Chem. Phys. 15(14): 4859-4869.
Köhler, C., et al. (2014) "Performance Loss of a Pt-Based Implantable Glucose Fuel Cell in Simulated Tissue and Cerebrospinal Fluids" ChemElectroChem, 1(11), pp. 1895-1900.
Lacour, S. P., et al. (2016) "Materials and technologies for soft implantable neuroprostheses." Nat. Rev. Mater. 1: 16063, 14 pages.
Mano, N., et al. (2003) "Characteristics of a Miniature Compartmentless Glucose-O2 Biofuel Cell and Its Operation in a Living Plant." J. Am. Chem. Soc. 125(21): 6588-6594.
Minev, I. R., et al. (2015) "Electronic dura mater for long-term multimodal neural interfaces." Science 347(6218): 159-163.
Pankratov, D., et al. (2014) "Hybrid electric power biodevices" ChemElectroChem, 1(11), pp. 1798-1807.
Payne, S.C., et al. (2018) "Bioelectric neuromodulation for gastrointestinal disorders: effectiveness and mechanisms" Nature Reviews Gastroenterology & Hepatology, pp. 89-105.
Rapoport, B.I., et al. (2012) "A glucose fuel cell for implantable brain-machine interfaces" PloS one, 7(6), p. e38436. 15 pages.
Reuillard, B., et al. (2013) "High power enzymatic biofuel cell based on naphthoquinone-mediated oxidation of glucose by glucose oxidase in a carbon nanotube 3D matrix." Phys. Chem. Chem. Phys. 15(14): 4892-4896.
Ten Vaarwerk, I.A. et al. (1998) "Spinal cord stimulation in chronic pain syndromes" Spinal cord, 36(10), p. 671-682.

(56) References Cited

OTHER PUBLICATIONS

Wang, S. F., et al. (2007). "Design of carbon paste biosensors based on the mixture of ionic liquid and paraffin oil as a binder for high performance and stabilization" Electrochem. Commun. 9(4): 807-812.

Jeerapan, I. et al. (2018) "Fully edible biofuel cells" Journal of Materials Chemistry B, vol. 6, pp. 3571-3578.

Jeerapan, I. et al. (2019) "On-Body Bioelectronics: Wearable Biofuel Cells for Bioenergy Harvesting and Self-Powered Biosensing" Advanced Functional Materials, 2019, 1906243, 18 pages.

Sales, F.C., 2013. An intravenous implantable glucose/dioxygen biofuel cell with modified flexible carbon fiber electrodes. Lab on a Chip, 13(3), pp. 468-474.

Zebda, A., et al, 2013. Single glucose biofuel cells implanted in rats power electronic devices. Scientific Reports, 3, p. 1516.

USPTO Non-Final Office Action mailed Aug. 15, 2024, U.S. Appl. No. 18/429,290, 14 pages.

\* cited by examiner

IMPLANTABLE, BIOFUEL CELLS FOR SELF-CHARGING MEDICAL DEVICES

CROSS-REFERENCE TO RELATED APPLICATIONS

This patent document is a 371 National Phase Application of International Application No. PCT/US2019/061537, filed on Nov. 14, 2019, which claims priority to and benefits of U.S. Provisional Patent Application No. 62/767,389 entitled "SELF- RECHARGING CATHETER-BASED BIOFUEL CELL DEVICES" filed on Nov. 14, 2018. The entire contents of the aforementioned patent applications are incorporated by reference as part of the disclosure of this patent document

TECHNICAL FIELD

This patent document relates to biofuel cell technology.

BACKGROUND

A fuel cell is a device that converts chemical energy from a substance (e.g., referred to as a fuel) into electrical energy (e.g., electricity). Generally, the energy conversion includes a chemical reaction with oxygen or another oxidizing agent. For example, hydrogen is among a common fuel, and hydrocarbons such as natural gas and alcohols can also be used in fuel cells. For example, fuel cells differ from batteries in that they require a constant source of fuel and oxygen to operate. A fuel cell can produce electricity continuously provided the fuel and oxygen inputs are supplied to the fuel cell.

SUMMARY

Disclosed are devices, systems, and methods for implantable biofuel cells integrable in a medical device to extract energy from a substance in a biological environment providing a fuel to a fuel cell.

In some aspects, an implantable biofuel cell device for extracting energy from a biological fluid includes a substrate, including (i) a first compartment having a first hollow interior portion and (ii) a second compartment having a second hollow interior portion, the second hollow interior portion separated from the first hollow interior portion, wherein the substrate includes one or more openings into each of the first hollow interior portion and the second hollow interior portion; an anode assembly, including (i) a first electrode disposed in the first hollow interior portion of the substrate and (ii) a functionalization material disposed on or integrated with the first electrode proximate the one or more openings, wherein the functionalization material includes a catalyst to facilitate conversion of a substance in the biological fluid to a first product in an oxidative process that releases electrons captured at the first electrode; and a cathode assembly, including (i) a second electrode disposed in the second hollow interior portion of the substrate and (ii) a catalytic material to reduce an oxygenated substance in the biological fluid to a second product in a chemical reduction process in which the second product gains electrons, wherein, when the biofuel cell device is inserted in a tissue exposing the biofuel cell device to the biological fluid, the biofuel cell device is operable to extract electrical energy from the substance in the biological fluid across the anode assembly and the cathode assembly.

In some aspects, a biofuel cell device for extracting energy from a biological fluid includes an anode assembly comprising: a first hollow elongated element, a first substance at least partially disposed inside the first hollow elongated element and that is at least partially electrically conductive, a first electrically conductive elongated element at least partially disposed inside the first hollow elongated element and coupled with the first substance, wherein the first hollow elongated element has at least one opening in its surface to expose at least a portion of the first substance; and a cathode assembly comprising: a second hollow elongated element, at second substance at least partially disposed inside the second hollow elongated element and that is at least partially electrically conductive, a second electrically conductive elongated element at least partially disposed inside the second hollow elongated element and coupled with the second substance, wherein the second hollow elongated element has at least one opening in its surface to expose at least a portion of the second substance, wherein the biofuel cell device to is operable to facilitate conversion of a substance in the biological fluid to a first product in an oxidative process that releases electrons captured at the first electrically conductive elongated element of the anode assembly and to reduce an oxygenated substance in the biological fluid to a second product in a chemical reduction process in which the second product gains electrons, thereby extracting energy from the substance in the biological fluid across the anode and the cathode assemblies.

In some aspects, a self-charging medical device includes a catheter comprising a first elongated tube and a second elongated tube coupled to the first elongated tube at one or more coupling positions along a longitudinal side of the first and second elongated tubes, the first elongated tube including a first compartment having a first hollow interior portion and a plurality of openings from an outer surface of the first elongated tube into the first hollow interior portion, the second elongated tube including a second compartment having a second hollow interior portion and a plurality of openings from an outer surface of the second elongated tube into the second hollow interior portion, wherein the second hollow interior portion is separated from the first hollow interior portion, and wherein the first and second elongated tubes include a bendable material; and a biofuel cell integrated in the catheter and comprising an anode assembly disposed in the first elongated tube and a cathode assembly disposed in the second elongated tube, the biofuel cell operable to extract electrical energy from a substance in a biological fluid across the anode assembly and the cathode assembly to supply the extracted electrical energy for the catheter. The anode assembly includes a first wire and a first substance, the first wire and the first substance disposed within the first hollow interior portion, wherein the first substance is coupled to at least a portion of the first wire proximate the plurality of openings of the first elongated tube, and wherein the first substance includes a functionalization material comprising a catalyst to facilitate conversion of the substance in the biological fluid to a first product in an oxidative process that releases electrons captured at the first wire. The cathode assembly includes a second wire and a second substance, the second wire and the second substance disposed within the second hollow interior portion, wherein the second substance is coupled to at least a portion of the second wire proximate the plurality of openings of the second elongated tube, and wherein the second substance includes a catalytic material to reduce an oxygenated substance in the biological fluid to a second product in a chemical reduction process in which the second product gains electrons.

In some embodiments, the biofuel cell is integrated with a catheter, such as a spinal cord catheter. In some implementations, a catheter-based fuel cell device uses cerebrospinal fluid (CSF) as a source of fuel, e.g., which enables the catheter-based fuel cell device to bypass an impulse pulse generator required for spinal cord stimulation by conventional spinal cord catheters. In some embodiments, the biofuel cell comprises an anode used to oxidize the biofuel (e.g., glucose or lactate in some implementations) and a cathode adapted to reduce a chemical substance, e.g. oxygen, generating electrical energy that can be used an electrical output for the integrated medical device. In some implementations of a spinal cord catheter-based biofuel cell device, for example, the device can direct current in the dorsal column or dorsal horn of the spinal cord to cause increased gamma-aminobutyric acid (GABA) neurotransmitter, e.g., resulting in decreased peripheral-to-central pain transmission. In this patent document, the terms "fuel cell" and "biofuel cell" may be used interchangeably. Example applications of the disclosed implantable biofuel cell-powered medical devices are envisioned to be used for treating refractory chronic pain through spinal cord neurostimulation, and in the treatment and management of conditions related to depression, acute pain, spinal cord paralysis, autonomic disorders, obesity, Tourette syndrome, and deafness, among others.

The subject matter described in this patent document can be implemented in specific ways that provide one or more of the following features.

DETAILED DESCRIPTION

Figure 1A:
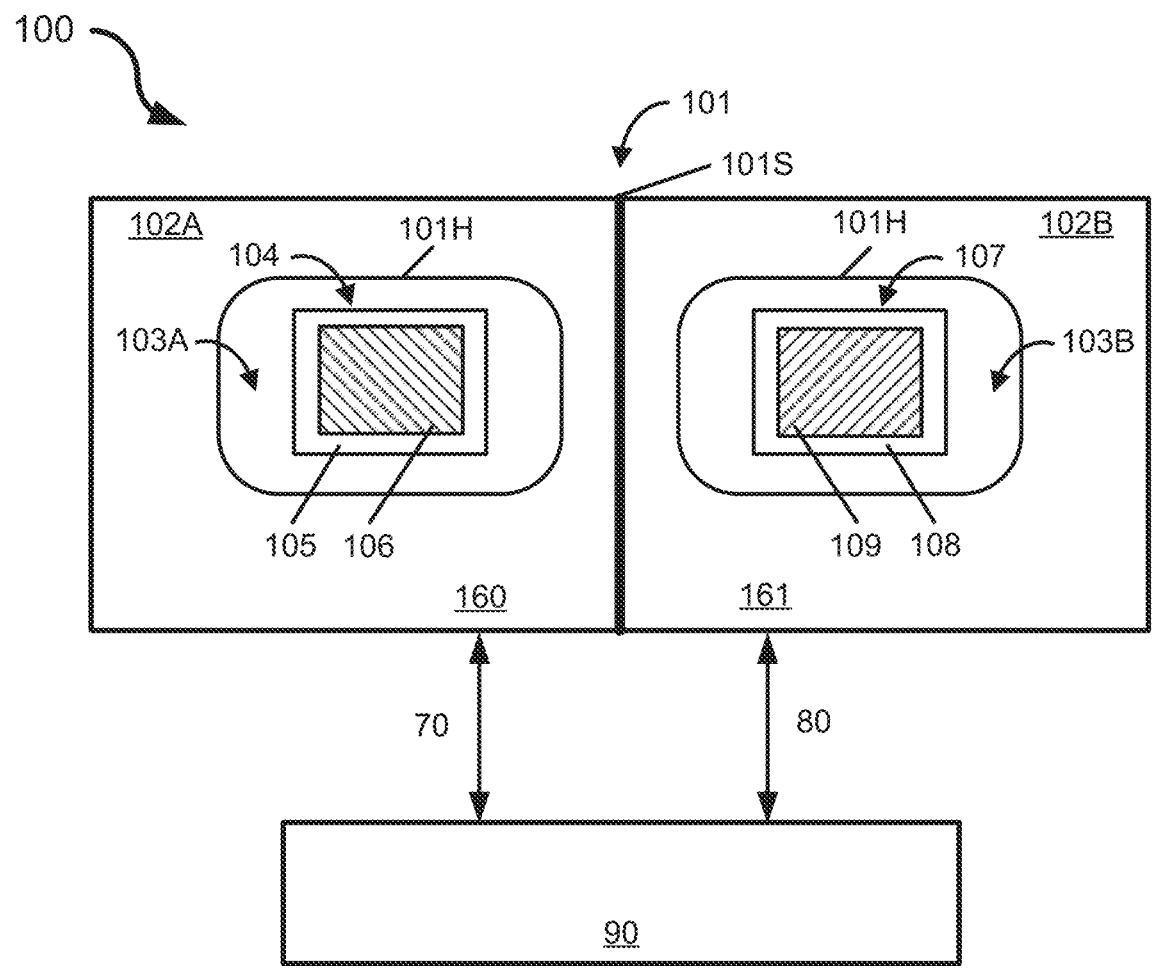
FIG. 1A shows a diagram of an example embodiment of an implantable biofuel cell device in accordance with the present technology.

Implantable bioelectronics has opened fascinating opportunities for biomedical applications, including personalized diagnostic and therapeutic purposes, e.g., including pain management. Yet, in order to drive such systems, a significant amount of power is needed to stimulate the electronics. Special requirements are often needed for the power source due to the emerging technologies and techniques used, especially when optimizing a usable battery. These challenges have hindered widespread adoption of new technologies for therapeutic treatments, particularly in pain management.

Take for example, devices for spinal cord stimulation. Currently, approximately 140 spinal cord neuromodulation devices are implanted for pain therapy every day. Spinal cord stimulation (SCS) involves using an electrical generator that supplies current pulses to a targeted spinal cord location. Besides applications for pain management, SCS can also be used, for example, to study the effects of Parkinson's disease and angina pectoris in affected patients. The SCS electrodes can be inserted by laminectomy or percutaneously. Although SCS can efficiently attenuate chronic pain in a large portion of the population (e.g., 50-70%), implementation of devices for SCS remains a challenge as it mandates a viable energy source which depends on an implanted battery and is capable of driving the electrical circuits used for the SCS. Typical energy-storage devices rely on re-charging and operation under non-physiological conditions. In addition, flexible and implantable batteries are very challenging to miniaturize. Moreover, it is highly desirable to avoid additional surgeries to replace such implanted energy devices. These factors add to the difficulties in the implementation of devices for SCS.

Despite attractive advantages of energy-harvesting devices, very few reports exist on the utilization of bioenergy available in cerebrospinal fluids (CSF) from the brain or spinal cord. However, to date, there are no reports on any implantable medical devices that have the capabilities of energy-harvesting and actuation functionality of the medical device powered by the energy-harvesting, e.g., such as electrical pulse generation, which could be used for spinal cord stimulation.

Disclosed are devices, systems, and methods for implantable biofuel cells capable of being integrated in a medical device to extract energy from a substance in a biological environment for providing a self-charging medical device.

Some example embodiments of the implantable biofuel cells described herein include flexible and integrated bioenergy-harvesting and spinal cord stimulating implant devices. Biofuel cells (BFCs) such as enzymatic biofuel cells can convert biochemical energy contained in metabolites, such as glucose or lactate, into electrical energy via biologically safe catalytic reactions. BFCs can harvest bioenergy from a biofuel present in biological fluids, ranging from blood to sweat or tears. The disclosed BFCs are integrated with bioelectronic devices, which can seamlessly integrate the functions of energy conversion and energy storage for the bioelectronic device. In some example embodiments, an implantable biofuel cell-integrable self-charging medical device can include miniaturized electrode designs which provide suitable bioelectronics-to-spinal cord interfaces, as described in further detail below. The example bioelectronic devices disclosed herein can harvest energy from biofuels in various implementations, such as lactate and glucose present in the cerebrospinal fluid, for example, and deliver electrical pulses for spinal cord stimulation.

Also disclosed are results of experimental implementations of example embodiments of a biofuel cell-integrated self-charging catheter device, which can be used for spinal cord stimulation for pain treatment. As discussed below, the example results showed that the waveforms of electrical pulses, supplied by the example BFC energy harvester, can effectively lessen chronic neuropathic pain in animal models. Also, for example, the superior efficiency of energy harvesting can be observed in the high-energy mode, e.g., by combining dual platforms of the seamless synergy of an energy-conversion BFC and an energy-storage capacitor. For example, the bipole lead and engineered materials of the example bioelectronic device concurrently behave as a completely integrated hybrid energy device that can deliver high power output during the discharge for spinal cord electrical stimulation tasks. The capacitance of the implantable biodevices described herein can unceasingly recharge through the natural recirculating energy-harvesting process. This self-charging capability addresses the limitations of the local consumption and diffusion of biofuels. Self-powered devices in accordance with the disclosed technology can deliver useful waveforms for spinal cord stimulation. Example implementations described herein demonstrate that electrical pulses, supplied by the devices in accordance with the disclosed technology, can be used for spinal cord stimulation that may effectively lessen chronic neuropathic pain in subjects, as shown in the example animal models.

Various example embodiments of self-charging medical devices integrated with biofuel cell devices in accordance with the present technology are described.

FIG. 1A shows a diagram of an example embodiment of an implantable biofuel cell device for providing a self-powered, self-charging medical device in accordance with the present technology, labeled device 100. The device 100 includes a substrate 101, which includes a first compartment 102A having a first hollow interior portion 103A and a second compartment 102B having a second hollow interior portion 103B. The substrate includes a separation 101S between the first hollow interior portion 103A of the first compartment 102A and the second hollow interior portion 103B of the second compartment 102B. In some embodiments, for example, the separation 101S can include a wall structure that is part of one or both of the first compartment 102A and the second compartment 102B. In some embodiments, the separation 101S can include a separate structure that connects at least a portion of the first compartment 102A with the second compartment 102B. The substrate 101 includes one or more openings 101I1 into each of the first hollow interior portion 103A and the second hollow interior portion 103B.

The device 100 includes an anode assembly 104 that includes an anode electrode 105 disposed in the first hollow interior portion 103A of the substrate 101. The anode assembly 104 can be disposed in the first hollow interior portion 103 proximate the one or more openings 101I1 of the first compartment 102A. The device 100 includes a cathode assembly 107 that includes a cathode electrode 108 disposed in the second hollow interior portion 103B of the second compartment 102B. In various implementations of the device 100, for example, the anode assembly 104 facilitates conversion of a biofuel substance in a surrounding biological fluid to a first product in an oxidative process that releases electrons captured at the anode electrode 105, and the cathode assembly 107 provides a catalyst that reduces an oxygenated substance in the biological fluid in a chemical reduction process, which extracts or harvests energy from the biofuel substance in the biological fluid for the device 100.

In some embodiments, for example, the anode assembly 104 includes a functionalization material 106 disposed on or integrated with at least a portion of the anode electrode 105. In some implementations of the device 100, for example, the functionalization material 106 can include a catalyst molecule to facilitate conversion of a substance in a biological fluid to a first product in an oxidative process that releases electrons captured at the anode electrode 105 of the anode assembly 104, thereby extracting energy from the substance in the biological fluid. In some embodiments of the device 100, for example, the functionalization material 106 can include a redox reaction mediator substance. FIG. 1A illustrates an example implementation where the functionalization material 106 is layer on the anode electrode 105.

The cathode assembly 107 provides a catalyst that reduces an oxygenated substance in the biological fluid in a chemical reduction process. In some embodiments, the cathode assembly 107 includes a catalytic material 109 that is disposed on or integrated with at least a portion of cathode electrode 108. FIG. 1A illustrates the catalytic material 109 as layer on the cathode electrode 108.

In some embodiments, the biofuel cell device 100 is electrically coupled to an electrical circuit 90 in an electrical configuration where the circuit is electrically coupled between the anode electrode and the cathode electrode. For example, the biofuel cell device 100 can include electrically conductive elements 160 and 161 that are coupled to or extensions of the anode electrode 105 and the cathode electrode 108. As shown in FIG. 1A, at least one of the electrically conductive elements 160 and 161 of the device 100, electrically coupled to the anode electrode 105 and the cathode electrode 108, respectively, which can be connected to the electric circuit 90 (e.g., which can be a switch, a control circuit, a sensor, or other circuit or can be included in a circuit-containing device) via electrical connection links 70 and/or 80. In various implementations, for example, the electric circuit 90 can affect control, measurement, and monitoring functions, among other functions, which are related to operation of the biofuel cell device 100. In some example implementations, the electrical circuit 90 can be included in an electronics unit of the integrated medical device, which can be used to regulate a switch to turn on or turn off to the biofuel cell device 100, and/or to control the amount current to flow through the biofuel cell device 100. In such implementations, the electronics unit can be used to control the electrical parameters of the medical device integrated to the biofuel cell device 100, e.g., such as amplitude, frequency, current level, wave forms, etc.

In some embodiments, the biofuel cell device is integrated with or structured as a medical device, such as a catheter. In some embodiments, the substrate can include two hollow tubes, coupled to each other, with an array of the openings to expose the hollow interior of each of the two hollow tubes, within which the anode assembly and the cathode assembly are disposed.

Figure 1B:
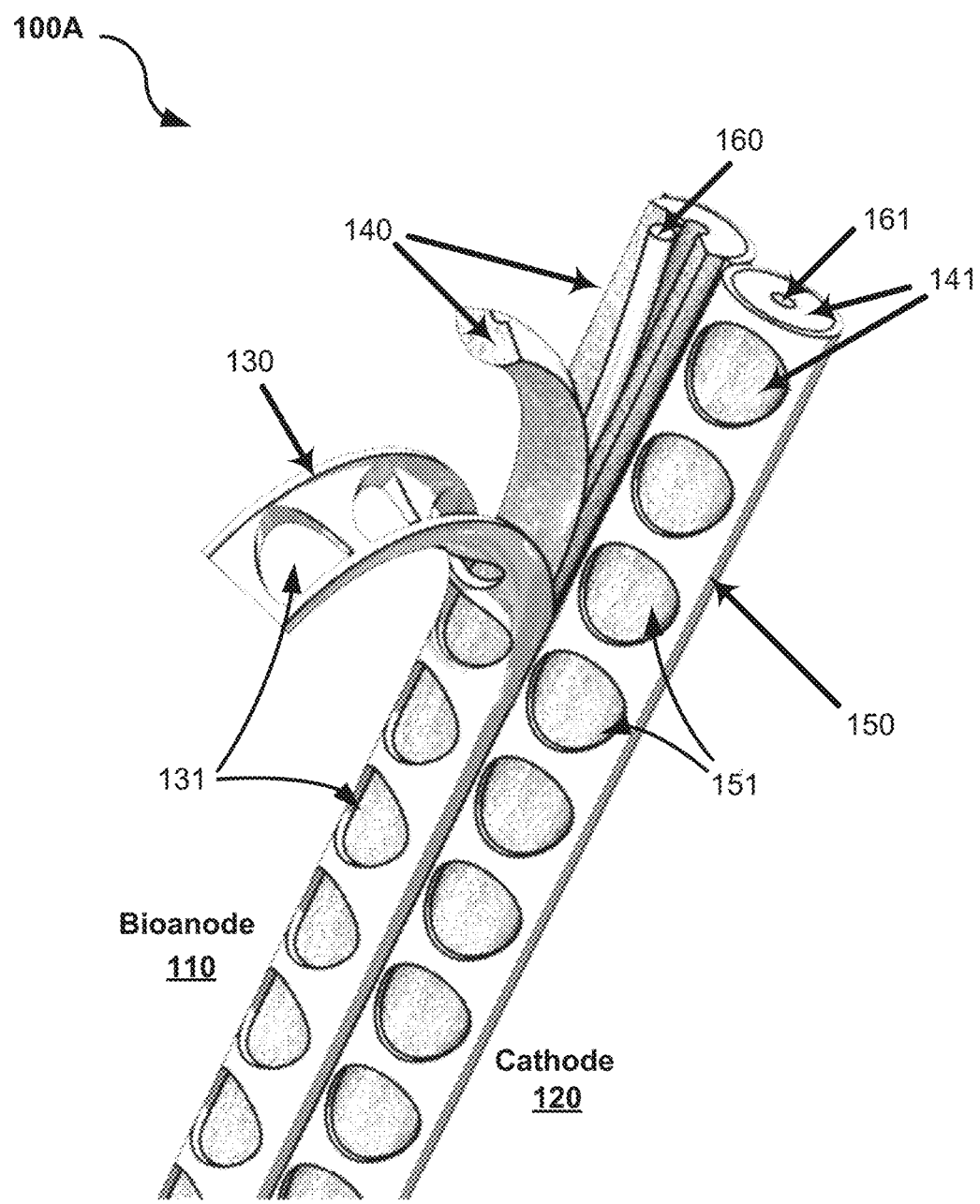
FIG. 1B shows an illustration of an example embodiment of an implantable biofuel cell device in accordance with the present technology, depicting the electrode composition at the anode and cathode assemblies.

FIG. 1B shows a diagram illustrating a perspective view of an example embodiment of the implantable biofuel cell device 100, labeled as device 100A. The device 100A includes anode contingent 110 (also referred to as anode 110, bioanode 110, or electrode 110) and cathode contingent 120 (also referred to as cathode 120 or electrode 120). In this example, the bioanode 110 includes an elongated hollow element 130, e.g., a tube, having at least one opening 131 located, e.g., on a side of the elongated hollow element 130. The opening(s) 131 can have any shape (e.g., circular, rectangular, arbitrary), and any size. The cathode 120 includes an elongated hollow element 150, e.g. a tube, having at least one opening 151 located, e.g., on a side of the elongated hollow element 150. The opening(s) 151 can have any shape (e.g., circular, rectangular, arbitrary), and any size. The elongated hollow elements 130 and 150 are configured to separate their respective interior regions so as to separate an anode and cathode of the biofuel cell device 100A. For example, in some embodiments, the elongated hollow elements 130 and 150 are configured to separate the anode contingent 110 and the cathode contingent 120 by at least 5 Each of the elements 130 and 150 can have any cross-section shape including but not limited to the elliptical, circular, rectangular, polygonal, and or other shape capable of insertion in a desired region of tissue. For example, the cross-section shape and/or the size of each of the elements 130 and 150 can vary along the length of the elements 130 and 150, respectively. Element 130 can have length which is different from the length of the element 150. Element 130 can have variations of its cross-section shape and/or its size which are different from variations of the cross-section shape and/or the size of the element 150. In various embodiments, for example, the element 130 and/or the element 150 can be formed, e.g., of a polymer material such as polytetrafluoroethylene (PTFE), polyurethane, or polyethylene, among other materials. For example, the element 130 and/or the element 150 can be made, for example, from a material suitable for a medical catheter. In some embodiments, for example, Material of the element 130 can be different from the material of the element 150.

In the example embodiment shown in FIG. 1B, the elongated hollow element 130 of the bioanode 110 is at least partially filled with a material 140, which can be at least partially electrically conductive. For example, in some embodiments, the material 140 includes a material with an electrical resistivity of less than 100 Ωcm or electrical conductivity above 0.01 Ωcm$^{-1}$. In some embodiments, the material 140 can include, e.g., multi-walled carbon nanotubes (e.g., purity 95%, diameter 9.5 nm, length 1.5 μm) or a conductive polymer material. In some embodiments, the material 140 also includes enzyme molecules which can oxidize a substance (e.g., glucose, lactate, among other biofuel substances) in a biological fluid such as, for example, the cerebrospinal fluid. In example implementations where lactate is a target biofuel for the device 100A, the example enzyme contained in the material 140 can be, for example, lactate oxidase (LOx) enzyme that oxidizes lactate. In some embodiments, the material 140 also includes a redox mediator, e.g. 1,4-naphthoquinone (NQ), that improves electron conductivity within the material 140 (e.g., for electron or charge transfer to the anode electrode and/or the electrical wiring of the device 100A), which can help to increase power density of the device 100A. In some embodiments, material 140 can also have constituents that act as a binding material for the other constituents or components of the material 140. In some embodiments, material 140 is characterized by having a porous structure such that to allow access of the constituents of a biofluid, e.g. the cerebrospinal fluid, to the portions of the material 140 beyond its surface visible from the outside of the material 140. In implementations of the material 140 including the enzyme and/or redox mediator, the enzyme and/or redox mediator substances included in the material 140 are preferably spread over the volume of the material 140 beyond its surface visible from the outside of the material 140. The bioanode 110 includes an electrically conductive element 160, which can include a wire and/or be made of, e.g., platinum (Pt) or another metal or electrically conductive substance such as an electrically conductive polymer, which is at least partially in contact with the material 140. Element 160 can have a form of, for example, a wire, a strip, a mesh, or a fiber.

In the example embodiment shown in FIG. 1B, the elongated hollow element 150 of the cathode 120 is at least partially filled with a material 141, which can be at least partially electrically conductive. For example, in some embodiments, the material 141 includes a material with an electrical resistivity of less than 100 Ωcm or electrical conductivity above 0.01 S cm$^{-1}$. In some embodiments, material 141 can include, e.g., multi-walled carbon nanotubes (e.g., purity 95%, diameter 9.5 nm, length 1.5 μm) or a conductive polymer material, e.g., poly(3,4-ethylenedioxythiophene) (PEDOT). Material 141 also includes a catalyst which helps to reduce an oxygenated substance (e.g., oxygen). In some embodiments, the catalyst can be, e.g., platinum (Pt) or, e.g., bilirubin oxidase, among others. In some embodiments, material 141 can also include a redox mitigation compound, e.g., polychlorotrifluoroethylene (PCTFE), which is characterized by a relatively high oxygen solubility and helps mitigate effects of oxygen fluctuations in the environment of the device 100A. Material 141 can also have components which act as binding materials for the other components of the material 141. For example, PCTFE can play the role of such a binding component, where the binding component(s) can support structural integrity of the material 141. In various example embodiments, the material 141 is characterized by having a porous structure such that to allow access of the constituents of a biofluid, e.g., the cerebrospinal fluid, to the portions of the material 141 beyond its surface visible from the outside of the material 141. In implementations of the material 141 including the platinum catalyst and/or a redox mitigation compound such as PCTFE, the platinum and PCTFE compounds, for example, are preferably spread over the volume of the material 141 beyond its surface visible from the outside of the material 141. The cathode 120 includes an electrically conductive element 161, which can include a wire and/or made of, e.g., platinum or another metal or electrically conductive substance such as an electrically conductive polymer, which is at least partially in contact with the material 141. Element 160 can have a form of, for example, a wire, a strip, a mesh, or a fiber.

In various example embodiments, the material 140 can fill different percentage of the volume inside the element 130 which is available for the material 140. For example, material 140 can fill only the parts of the volume inside the element 130 which are adjacent to one or more of the openings 131 in the element 130. For example, material 140 can fill substantially the whole volume available for the material 140 inside the element 130.

Similarly, in various example embodiments, the material 141 can fill different percentage of the volume inside the element 150 which is available for the material 141. For example, material 141 can fill only the parts of the volume inside the element 150 which are adjacent to one or more of the openings 151 in the element 150. For example, material 141 can fill substantially the whole volume available for the material 141 inside the element 150.

Moreover, in various embodiments of the biofuel cell device 100A, the elongated hollow element 130 has a ratio of its length to its width measured at a point along the length of the element 130 which is at least 1.1. In some example embodiments of the biofuel cell device 100A, the elongated hollow element 130 has a ratio of its length to its width measured at a point along the length of the element 130 which is at least 2. In some example embodiments of the biofuel cell device 100A, the elongated hollow element 130 has a ratio of its length to its width measured at a point along the length of the element 130 which is at least 5. In some example embodiments of the biofuel cell device 100A, the elongated hollow element 130 has a ratio of its length to its width measured at a point along the length of the element 130 which is at least 10. In some example embodiments of the biofuel cell device 100A, the elongated hollow element 130 has a ratio of its length to its width measured at a point along the length of the element 130 which is at least 20. In some example embodiments of the biofuel cell device 100A, the elongated hollow element 130 has a ratio of its length to its width measured at a point along the length of the element 130 which is at least 50. In some example embodiments of the biofuel cell device 100A, the elongated hollow element 130 has a ratio of its length to its width measured at a point along the length of the element 130 which is at least 100. Notably, these example length-width ratios can be applied to the elongated hollow element 150 for various embodiments of the biofuel cell device 100A.

Figure 1C:
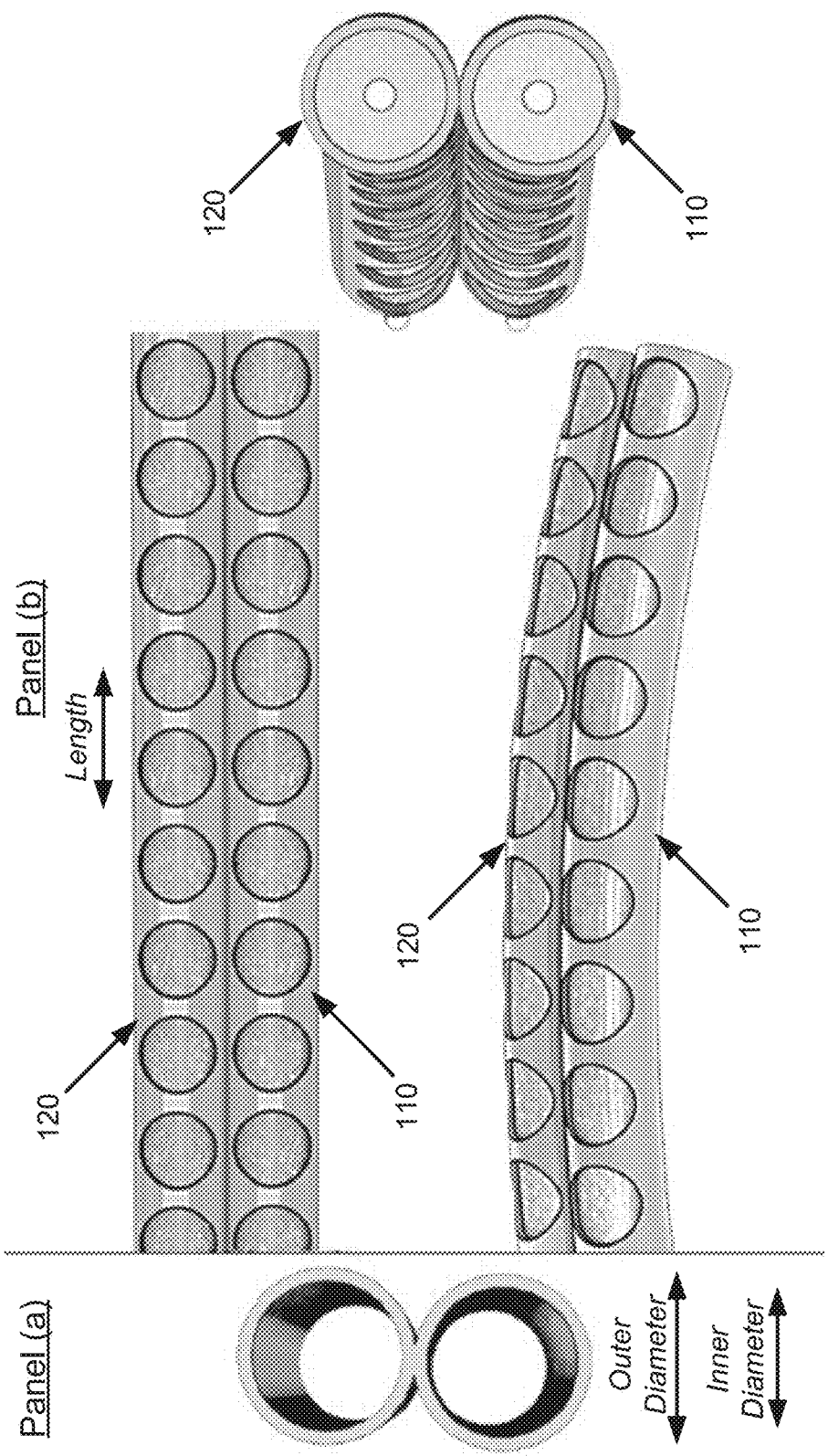
FIG. 1C shows an illustration the example embodiment of the implantable biofuel cell device shown in FIG. 1B, depicting various views of the anode and cathode contingents encased by a substrate.

FIG. 1C shows additional illustrations of the example implantable biofuel cell device 100A, depicting various views of the anode and cathode contingents encased by a substrate. The left panel (Panel (a)) illustrates a cross-sectional view of the example tubing used to make the elements 130 and 150 of an embodiment of the implantable biofuel cell device 100A. In some implementations, the diameter of the elements 130 and 150 includes 900 µm. The right panel (Panel (b)) illustrates the top view, side view, and longitudinal view of an embodiment of the implantable biofuel cell device 100A.

Figure 1D:
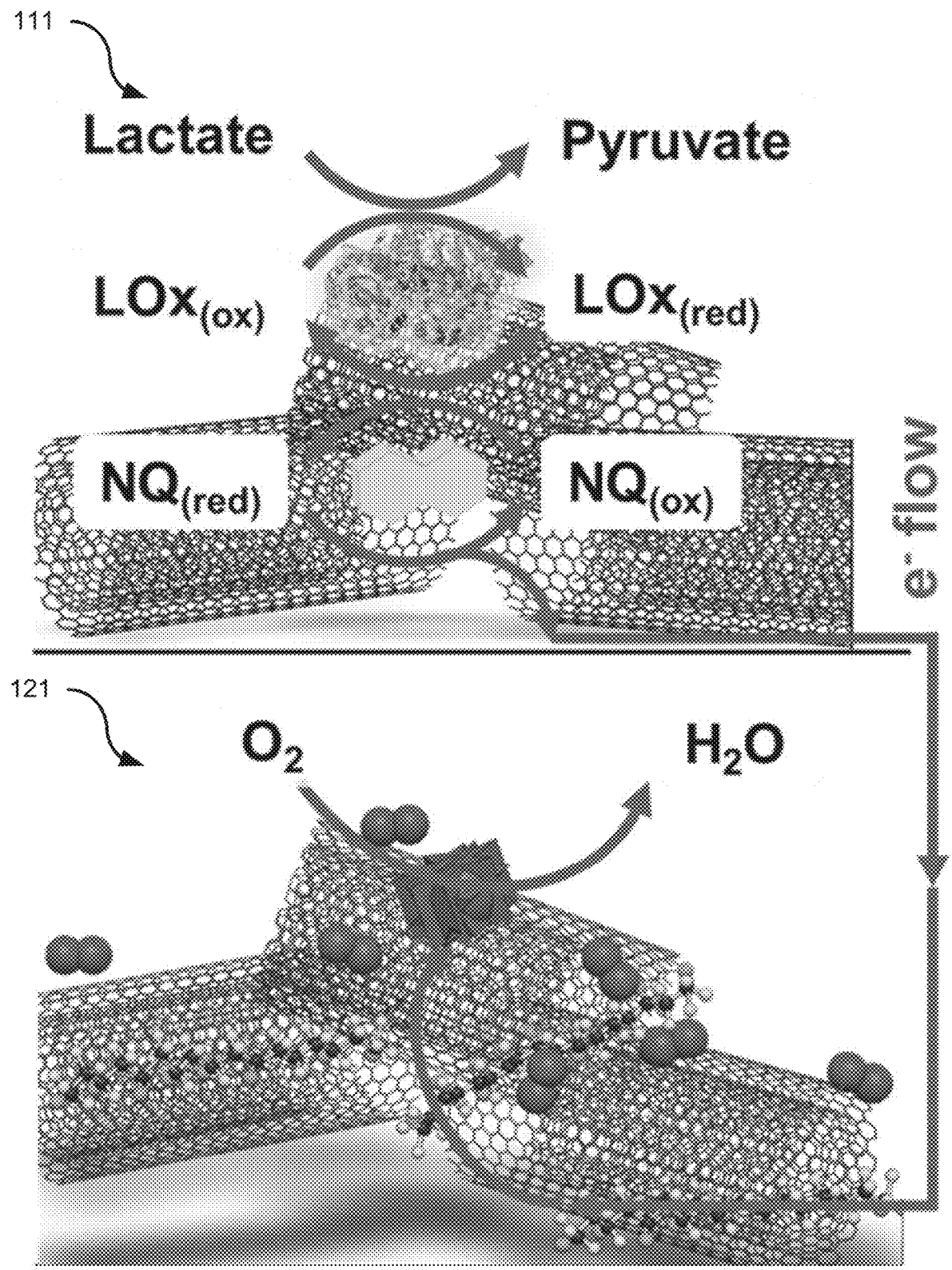
FIG. 1D shows a diagram depicting example electrochemical reactions occurring at the anode and cathode of an example embodiment of the biofuel cell device in accordance with the disclosed technology.

FIG. 1D shows a diagram of an example embodiment of the material 140 and/or material 141 that illustrates an example implementation of processes 111 and 121 taking place at the bioanode 110 and cathode 120 of the implantable biofuel cell device 100A, respectively. In the example implementation, the process 111 includes a reaction between lactate and lactate oxidase (LOx) that leads to oxidation of lactate to pyruvate and releases electrons which are captured at the anode 110. The oxidation of lactate can be assisted by the functionalized correspond LOx enzyme. Such an enzyme-catalyzed oxidation at the bioanode 110 can operate under mild conditions (e.g., normal physiological conditions). For a glucose-based biofuel cell, for example, lactate, pyruvate, and lactate oxidase (LOx) can be replaced by glucose, gluconolactone, and glucose oxidase (GOx), respectively. For glucose oxidation via the GOx-catalyzed oxidation at the glucose bioanode, for example, the glucose can provide the electrons and gluconolactone as a byproduct. Processes 111 includes, for example, electron shuttling from LOx to the carbon nanotubes using redox mediator NQ. For example, the example redox mediator NQ can provide a key function of assisting the electron shuttle process between the enzyme redox center (e.g., in LOx or GOx) and the electrode material (e.g., carbon nanotubes). An example of the role of the mediator can be described as the following events. The redox mediator ($NQ_{(ox)}$, oxidized form) accepts the electrons (generated from lactate via the oxidation); simultaneously, the mediator is converted into the reduced form (e.g., $NQ_{(red)}$, containing more electrons). Subsequently, the reduced form of the NQ mediator is reoxidized at the electrode, giving electrons to the electrode. While the electrochemical oxidation (e.g., process 111) occurs on the anode, the electrochemical reduction (e.g., process 121) occurs on the cathode. Process 121 include, for example, an oxygen-reduction reaction (ORR). In general, the electrocatalyst in the cathode (such as Pt, presented in process 121) can help the electroreduction of oxygen. The example of corresponding reaction is $O_2 + 4H^+ + 4e^- \rightarrow 2H_2O$.

Figure 1E:
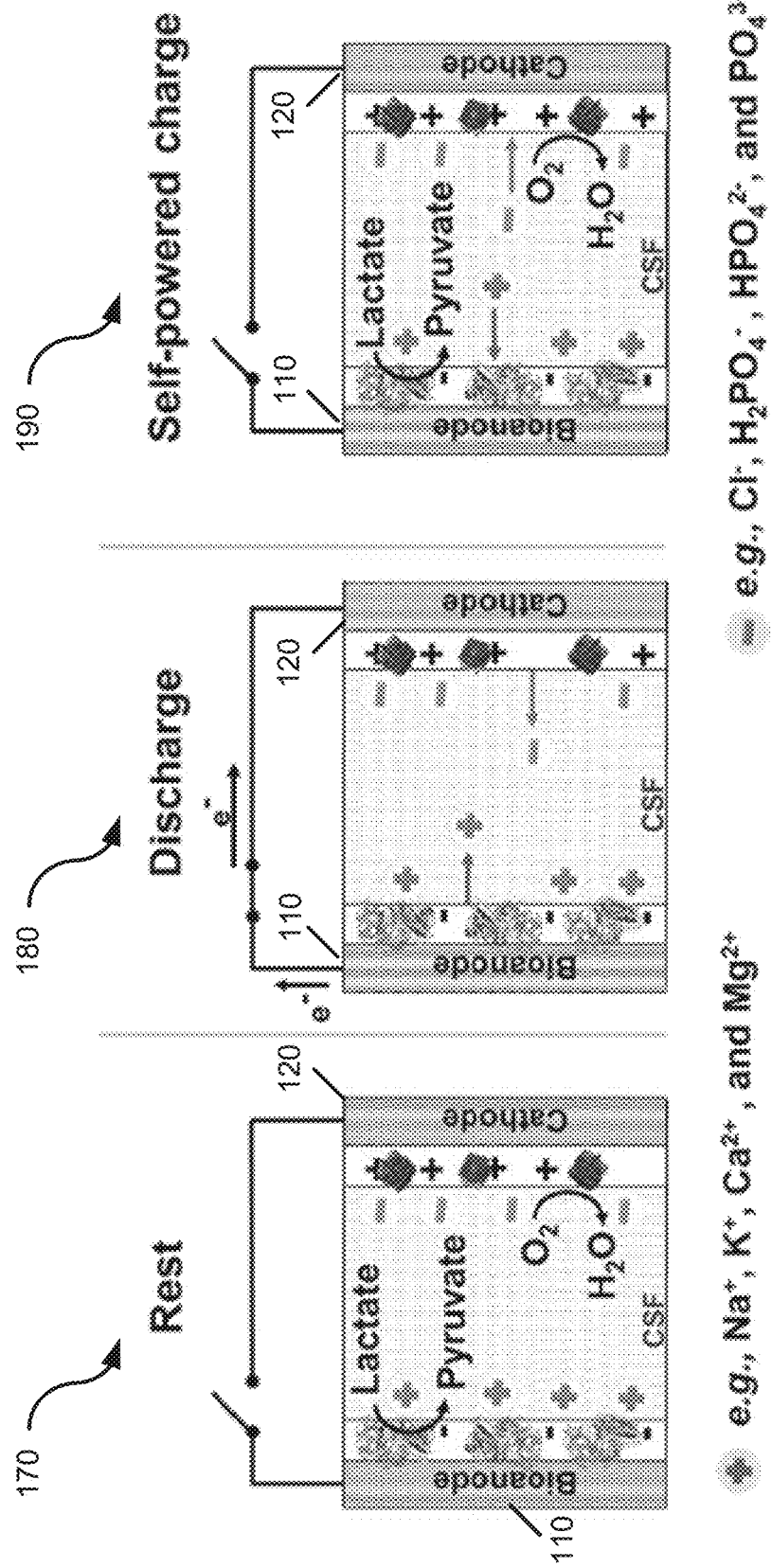
FIG. 1E shows a schematic representation of the stages in functioning of a self-charging capacitor, occurring on the example biofuel cell device of FIG. 1D.

FIG. 1E shows schematic diagrams representing stages in functioning of a self-charging capacitor, occurring on an example biofuel cell device in accordance with the disclosed technology. At stage 170, while the circuit is opened, the device is self-charged due to the electrochemically catalyzed fuel conversion at both electrodes 110 and 120. At stage 180, closing the circuit using, e.g., a switch connected to the elements 160 and 161 of the device 100 allows the current to flow, and the device is discharged for neurostimulation. At stage 190, the device performance is recovered through self-powered charging.

Figure 1F:
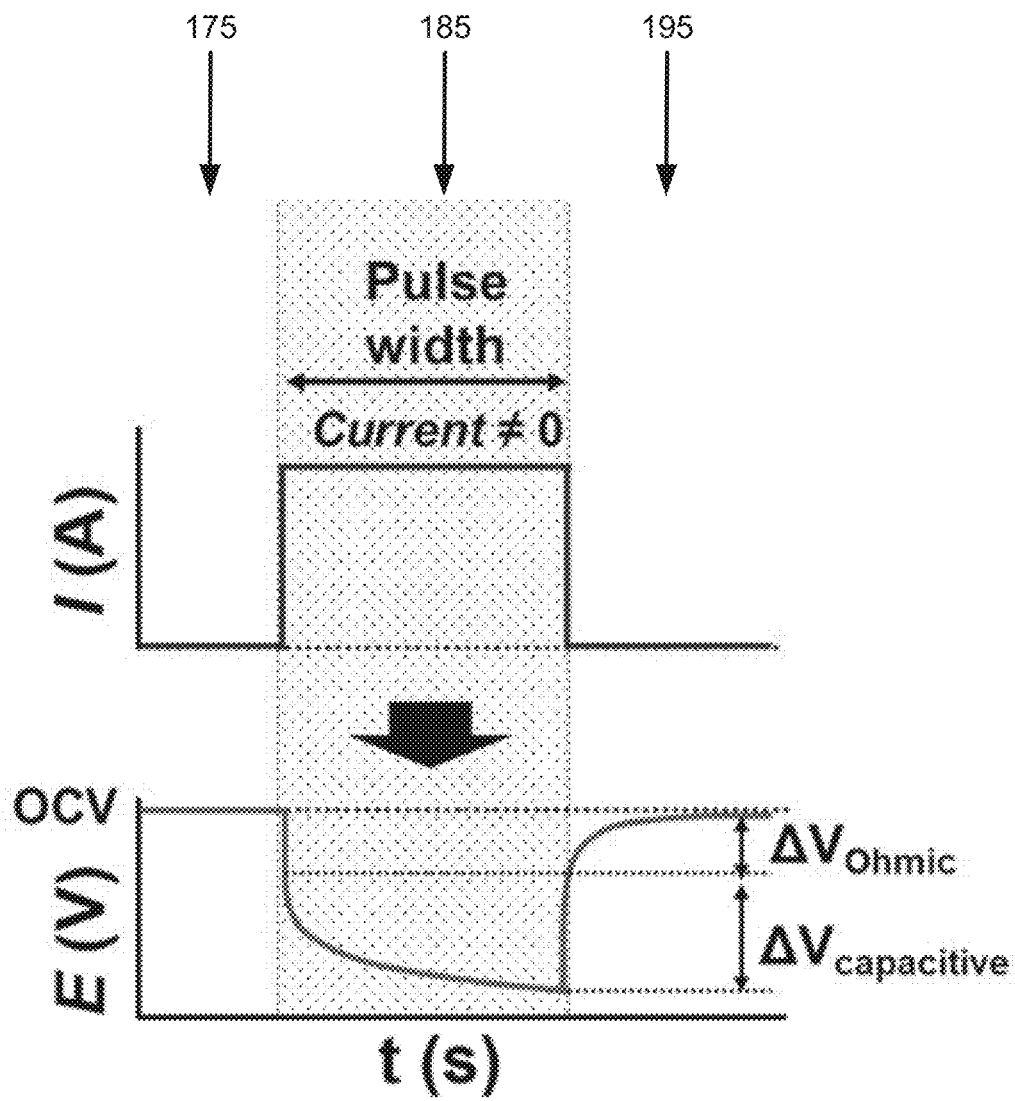
FIG. 1F shows an illustration of the voltage and current profiles created by an example biofuel cell device in accordance with the disclosed technology.

FIG. 1F shows an illustrative plot depicting an example of the voltage and current profiles created by an example biofuel cell device 110 in accordance with the disclosed technology during the stages 170, 180, and 190 illustrated in FIG. 1E. Profiles in the plot portion 175 correspond to the stage 170 where the example self-charging capacitor circuit is open (and at rest), profiles in the plot portion 185 correspond to the stage 180 where the example self-charging capacitor circuit is closed (and discharging), and profiles in the plot portion 195 correspond to the stage 190 where the example self-charging capacitor circuit is open again (and self re-charging).

During the "Rest" stage 170 (FIG. 1E), the open circuit voltage (OCV) of the biofuel cell device 100 is determined by the half reactions taking place at the electrodes 110 and 120. At the anode 110, the lactate oxidation reaction is equal to ~−0.2 mV vs Ag/AgCl. Conversely at the cathode 120, the oxygen reduction reaction is at ~−0.5 mV vs Ag/AgCl. When the circuit is open, the LOx enzyme at the anode 110 is oxidizing lactate to generate electrons and the platinum catalyst at the cathode is helping to reduce the oxygen to remove electrons. After some elapsed time, both electrodes are fully and oppositely charged, behaving like a two-plate capacitor. The excess charge at both electrodes is balanced by the electrolyte ions found in the cerebrospinal fluid (e.g., $Na^+$, $K^+$, $Ca^{2+}$, $Mg^{2+}$, $Cl^-$, $H_2PO_4^-$, $HPO_4^{2-}$, and $PO_4^{3-}$). These electrolyte ions migrate to their respective electrode and form an electrochemical double layer (EDL) at each of the electrodes 110 and 120. Similar to an electrical double layer capacitor (EDLC), the biofuel cell device 100 is electrostatically storing energy at an open circuit that can be used upon closure of the circuit.

During the "Discharge" stage 180 (FIG. 1E), upon closure of the circuit using, e.g., a switch connected to the elements 160 and 161 of the device 100, current flows from the electron-rich anode 110 to the electron-poor cathode 120 discharging the biofuel cell. Surfaces previously carrying charge are gradually neutralized, and the electrochemical double layers found at the electrodes 110 and 120 are dissipated throughout the solution, e.g., CSF. Therefore, the energy that was electrostatically stored in the device 100 prior to the stage 180 can be delivered in galvanostatic discharge pulses. Those pulses can be powerful enough to perform the spinal cord stimulation. Note that during the stage 180 the enzymes are still continuously converting the fuel substrates thus adding current to the one flowing due to the discharging of the accumulated charges.

Stage 190 ("Self-powered charge", FIG. 1E) allows the biofuel cell device 100 to self-charge through enzymatic reactions at the electrodes 110 and 120. During the stage 190 the device 100 is set to an open circuit mode by, e.g., opening the switch which was used to close the circuit during the stage 180. Opening the switch allows for the continuously-operating enzymes to reestablish the opposite charges and recreate the electrochemical double layers at the electrodes 110 and 120. This behavior allows the device 100 to operate as a self-rechargeable capacitor by simply opening and closing the circuit. The cycle of closing and opening the circuit can be frequently repeated with well-defined recharging periods (sub ms $pulse^{-1}$) to allow generation of high-current pulses.

Example uses of example embodiments of the implantable biofuel cell device 100 can include integration with a medical device and/or its implantation in a human body, such as in the spinal space, to, e.g., power a medical device electrically coupled to the device 100. Device 100 provides a useful power source for low-power implantable medical devices. Device 100 can be used, for example, to generate electrical pulses for treating refractory chronic pain through the spinal cord stimulation. Device 100 can operate under physiologic conditions, such as intra-body pH and temperature and can be employed for harvesting energy from biochemical constituents of biofluids such as cerebrospinal fluid which is repeatedly produced by the choroid plexus.

Figure 2A:
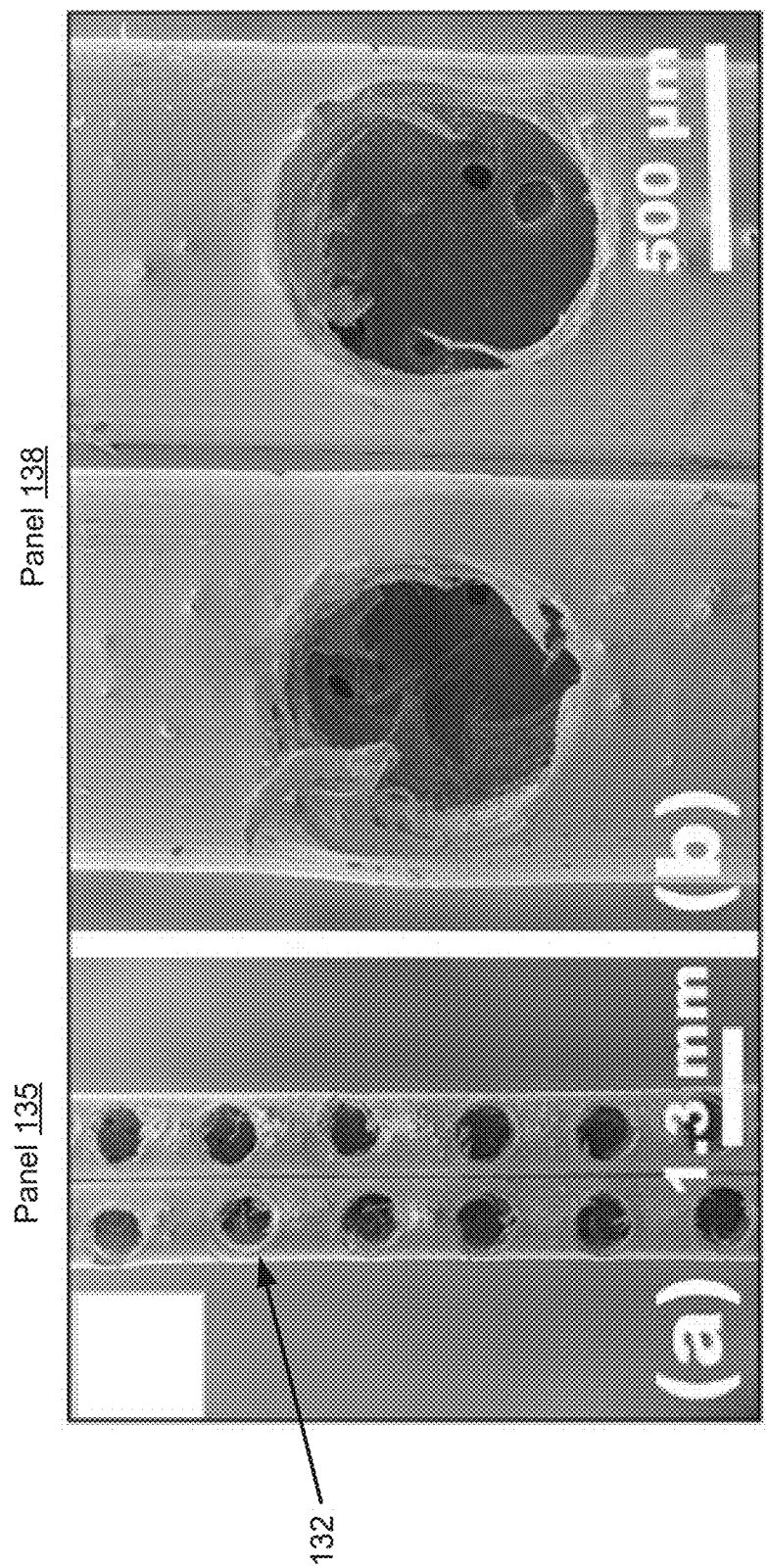
FIG. 2A shows scanning electron microscopy (SEM) images of hollow flexible tubes used for electrodes preparation for an example embodiment of the biofuel cell device.

FIG. 2A shows scanning electron microscopy (SEM) images of an implementation of an example implantable biofuel cell device, e.g. for providing a self-charging medical device such as a spinal cord catheter, which shows the dual hollow flexible tubes embodied as the elements 130 and 150 used for preparation of electrodes 110 and 120. Panel 135 of FIG. 2A shows a SEM image of the example dual hollow flexible tubes taken at a certain resolution, and panel 138 shows a zoomed-in SEM image of a smaller portion of the tubes taken at a higher resolution. One of the openings in the side of one of the tubes is shown by the arrow 232.

Figure 2B:
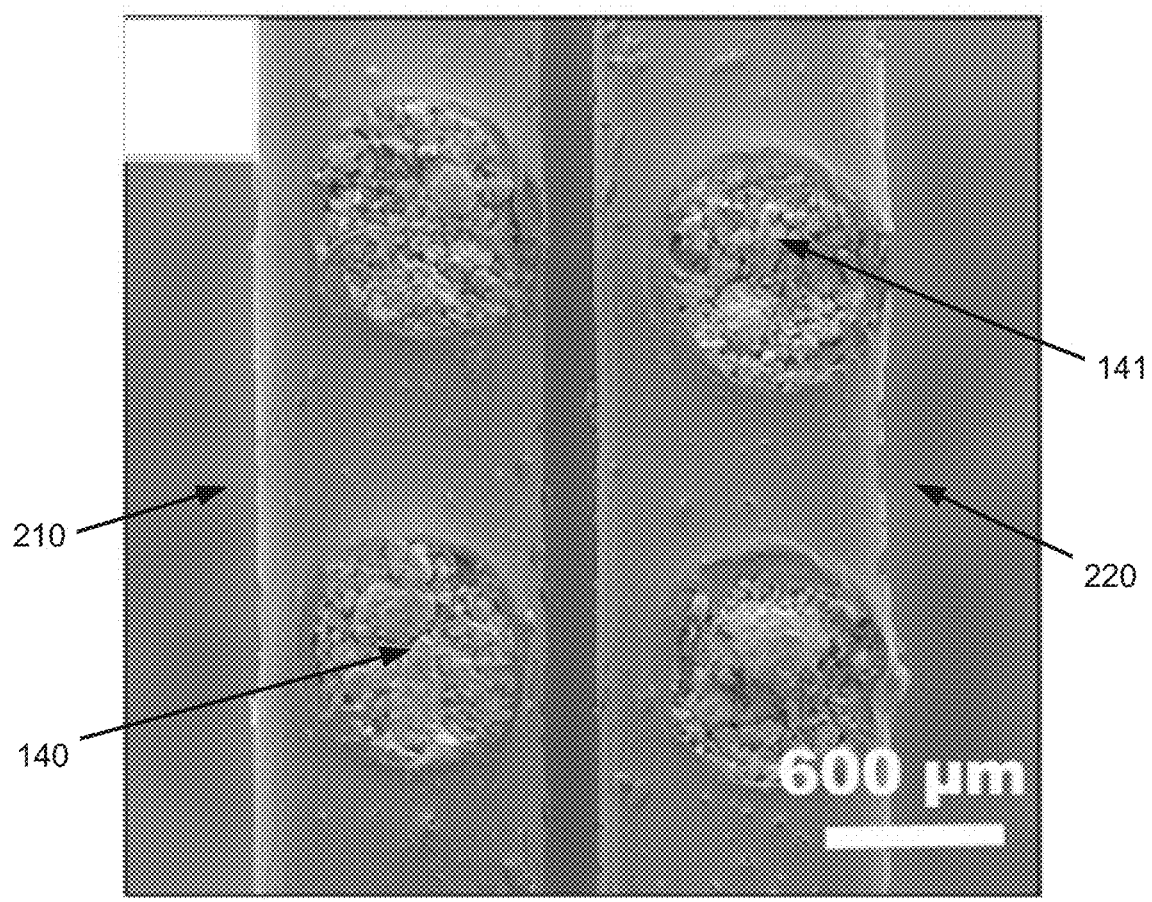
FIG. 2B shows a scanning electron microscopy (SEM) image of the electrodes packed with the active electrode materials for the example biofuel cell device shown in FIG. 2A.

FIG. 2B shows a scanning electron microscopy (SEM) image of the example implantable biofuel cell device shown in FIG. 2A, where the electrodes of the biofuel cell, labeled 210 and 220, packed with the active electrode materials 240 and 241, which include multi-walled carbon nanotubes in this example.

Figure 3A:
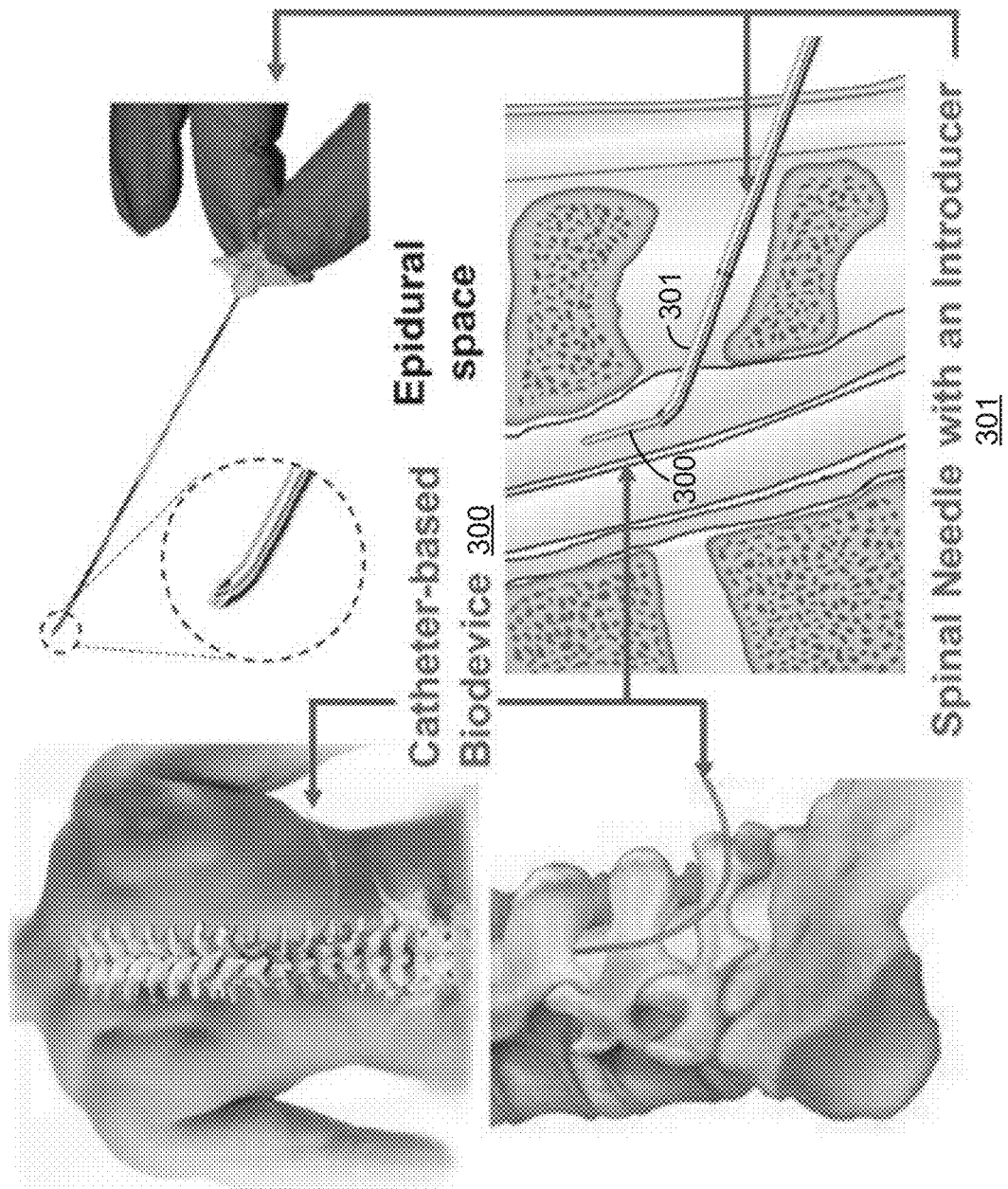
FIG. 3A shows an illustration of a catheter-based device being inserted into the epidural space.

FIG. 3A shows an illustration of a catheter-based biodevice 300 being inserted into the epidural space through a spinal needle with an introducer 301. A catheter-based device is generally a device in which a catheter, e.g. a medical catheter, is used as one of its elements or is used to make one of its elements; generally, the term "catheter" refers to a flexible tube or a flexible lead. In the case of the example device 300, a catheter, including a medical one, can be used, for example, to provide elements 130 and/or 150 to encase the bioanode 110 and cathode 120 of an example biofuel cell device 100A.

Figure 3B:
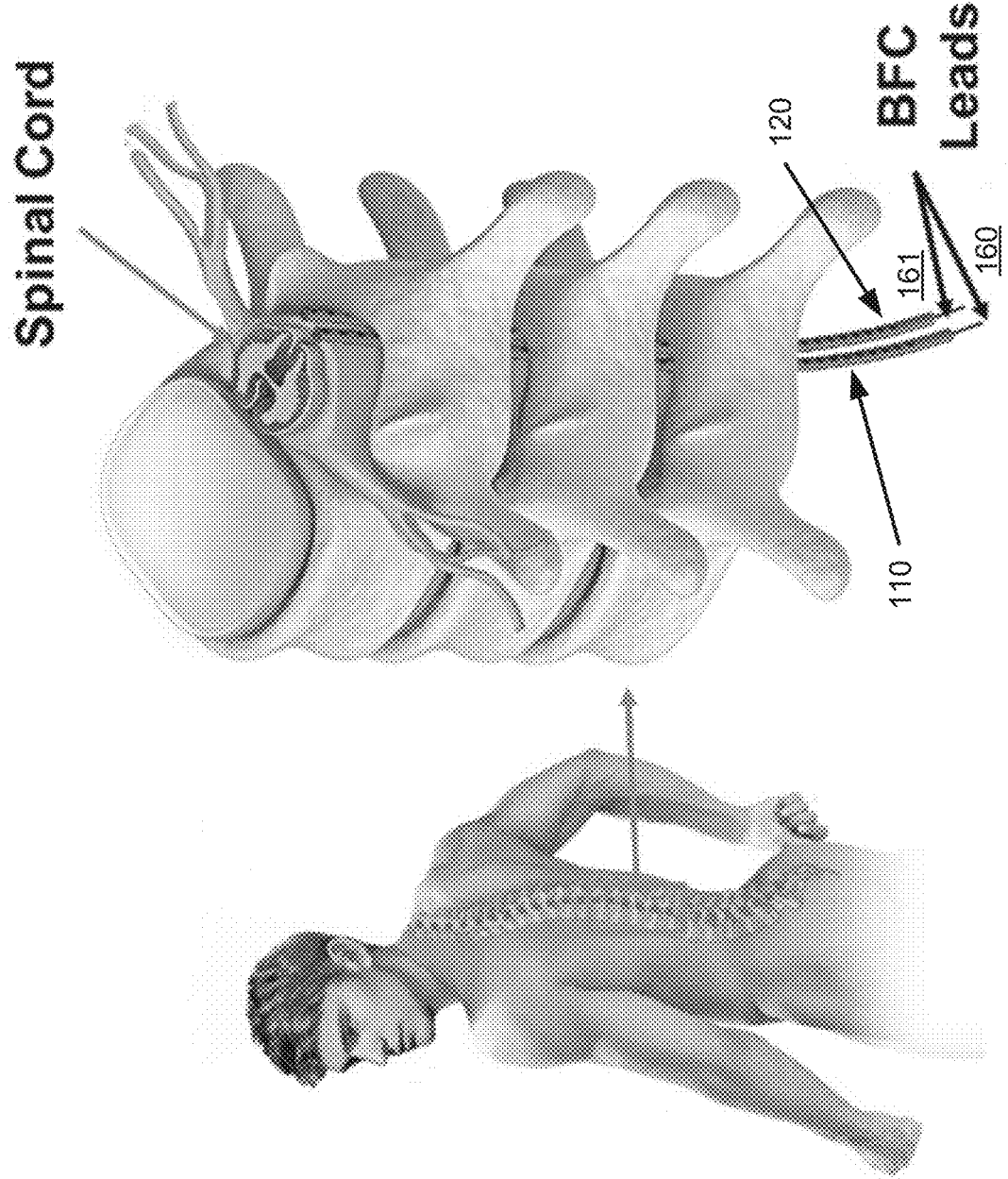
FIG. 3B shows a schematic representation of a catheter-based device implanted along the spinal subdural space.

FIG. 3B shows a schematic representation of an example embodiment of the biofuel cell device 100A configured as a medical catheter implanted along the spinal subdural space. The schematic illustrates how the elements 130 and 150 that encases the bioanode 110 and cathode 120 of the example biofuel cell device 100A can interface with the spinal cord tissue. The schematic also illustrates how the structure of the example embodiment of the biofuel cell device 100A can provide a degree of bendability for the biofuel cell device 100A sufficient for interfacing the biofuel cell device 100A with the spinal cord tissue. The bendability of the device is provided, at least in part, through a sufficiently high ratio of the length to the diameter of the elements 130 and 150, and/or a sufficiently high number of openings in the surfaces of the elements 130 and 150, and/or a sufficiently high bendability of the elongated elements 160 and 161, and/or a sufficient bendability and/or dispersion of the materials 140 and 141, and/or through a sufficiently high bendability of elements 130 and 150, or through a combination of one or more of the above features.

Figure 3C:
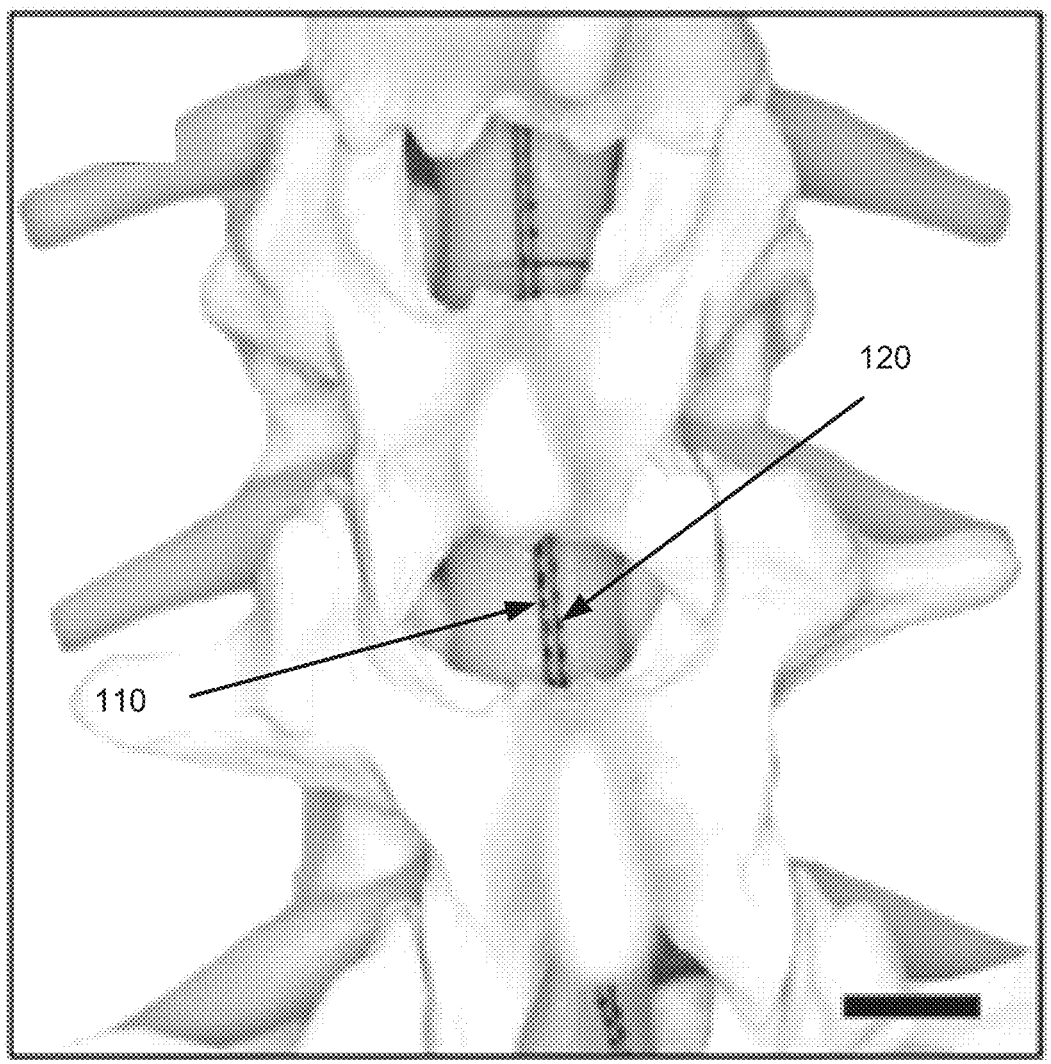
FIG. 3C shows an optical microscopy image of an implanted catheter-based fuel cell device in a spinal cord model.

FIG. 3C shows an optical microscopy image of an example implanted catheter-based biodevice inserted in a physical model of a spinal cord.

Figure 3D:
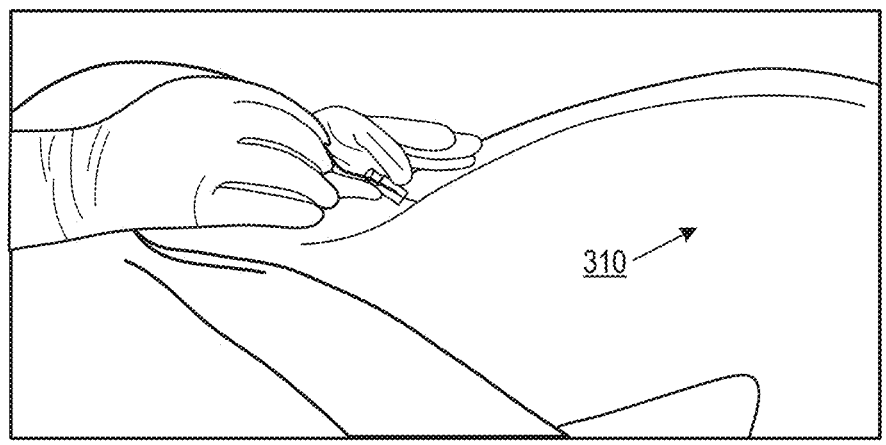
FIGS. 3D-3F show images depicting in-vivo implantation procedures of an example catheter-based biofuel cell device in a human cadaver model.
Figure 3E:
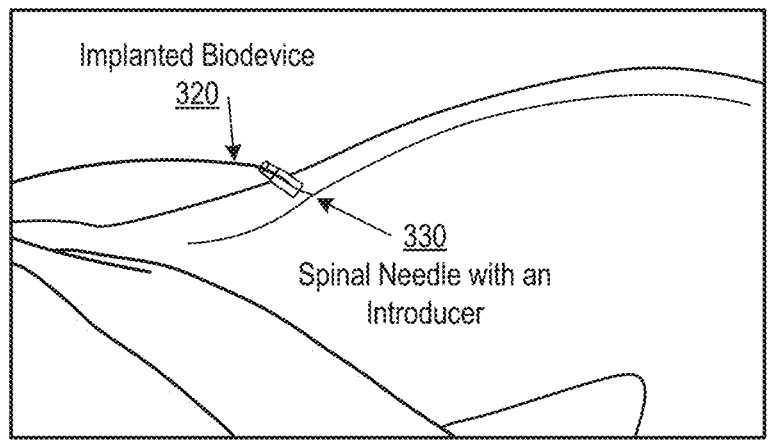
Figure 3F:
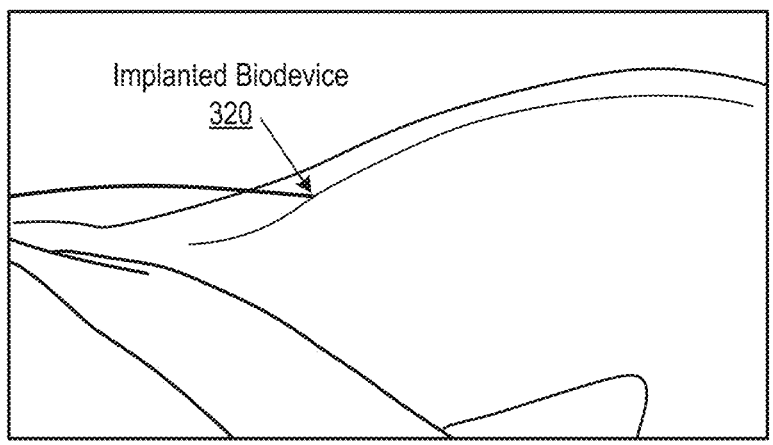

FIGS. 3D-3F show images of in-vivo implantation procedures of an example catheter-based biofuel cell device in accordance with the present technology being implanted in a human cadaver model. As shown in FIG. 3D, the image depicts the cadaver model 310. The image of FIG. 3E shows the example implanted catheter-based biodevice 320 being implanted by a spinal needle with an introducer 330. The image of FIG. 3F shows human cadaver model 310 after the example implanted catheter-based biodevice 320 was inserted via the spinal needle with an introducer.

Figure 3G:
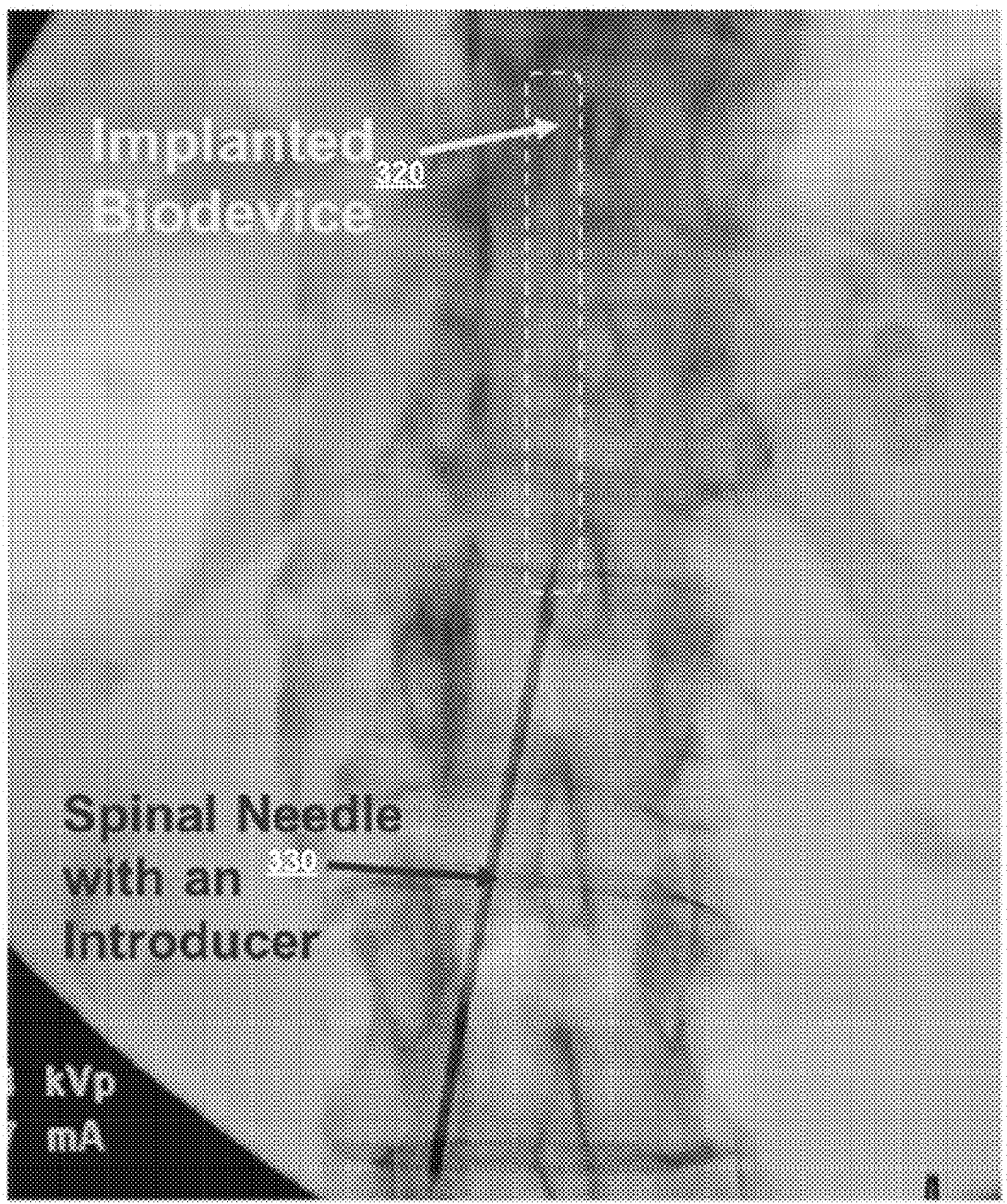
FIG. 3G shows a posteroanterior X-ray view of an example implanted catheter-based biofuel cell device and a spinal needle.

FIG. 3G shows a posteroanterior X-ray view of the example implanted catheter-based biofuel cell device 320 and spinal needle 330.

Example implementations were performed where electrochemical properties of an example embodiment of the implantable biofuel cell device 100 in accordance with the disclosed technology were investigated. The example BFC device was investigated at room temperature in a single chamber without any separating membrane. Batch experiments were performed.

Electrochemical experiments were carried out using a μAutolab Type II controlled by NOVA software (version 1.11). The power curves were obtained by scanning the voltage between the open circuit voltage (OCV) of the BFC to 0 V at a constant scan rate (e.g., such as 5 mV s$^{-1}$). A 0.5 M phosphate buffer solution was used as a supporting electrolyte. The total geometrical volume of both electrodes was used to normalize the volumetric density values.

Electrochemical properties of the electrodes of the example BFC device used in the experiment were investigated by observing electrochemical voltage-current profiles.

Figure 4A:
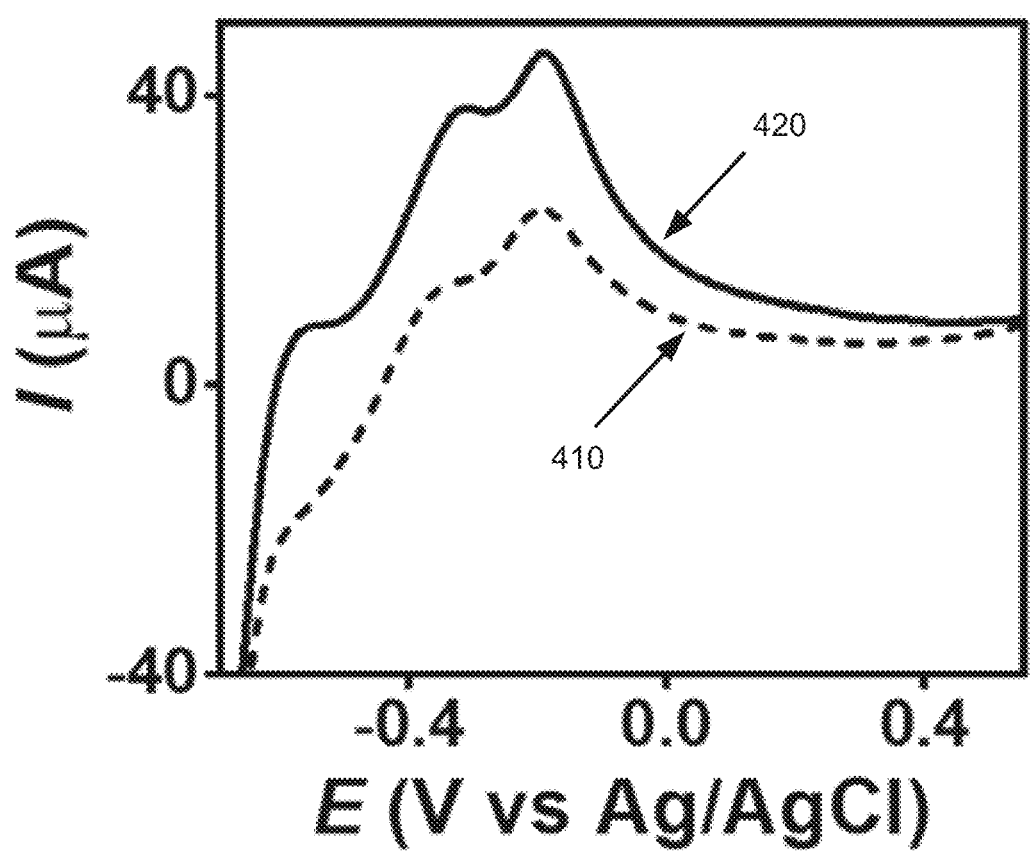
FIG. 4A shows linear sweep voltammograms (LSV) for the anode of an example embodiment of the biofuel cell device in accordance with the disclosed technology.

FIG. 4A shows linear sweep voltammograms (LSV) for the anode of the example BFC device in the absence and presence (dotted line 410 and solid line 420, respectively) of 2.8 mM lactate in 0.5 M phosphate-buffered saline containing potassium, PBS, (pH 7.4). The anode was scanned in 2.8 mM lactate with a linear sweep voltammogram (5 mV s$^{-1}$), revealing a catalytic onset around at −0.4 V (vs. Ag/AgCl) and the peak is near −0.2 V (FIG. 4A).

Figure 4B:
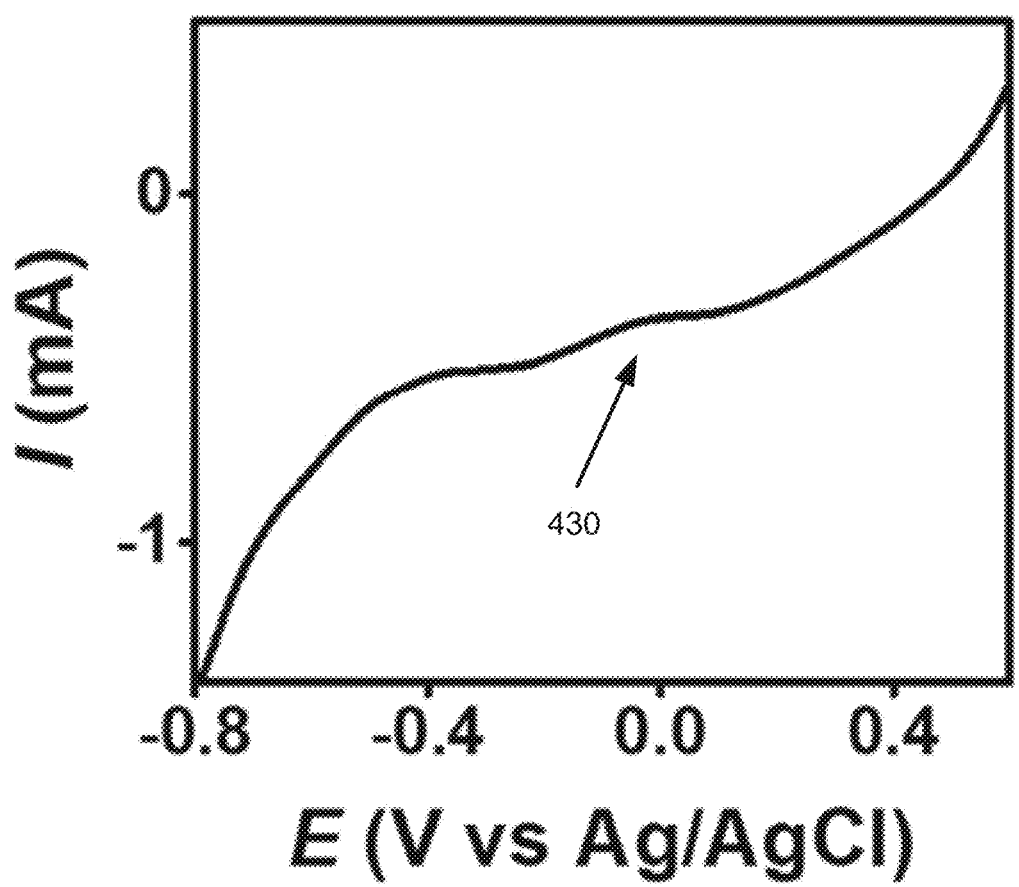
FIG. 4B shows linear sweep voltammogram (LSV) for the cathode of an example embodiment of the biofuel cell device in accordance with the disclosed technology.

Pt was selected as the catalyst in the cathode for oxygen reduction because it can catalyze the reaction with a low overpotential. FIG. 4B shows LSV 430 at the Pt-containing cathode of the example BFC device for $O_2$ reduction in 0.5 M PBS (pH 7.4). As depicted in the data plot, the start of the reduction at the cathode appears at +0.50 V.

Figure 4C:
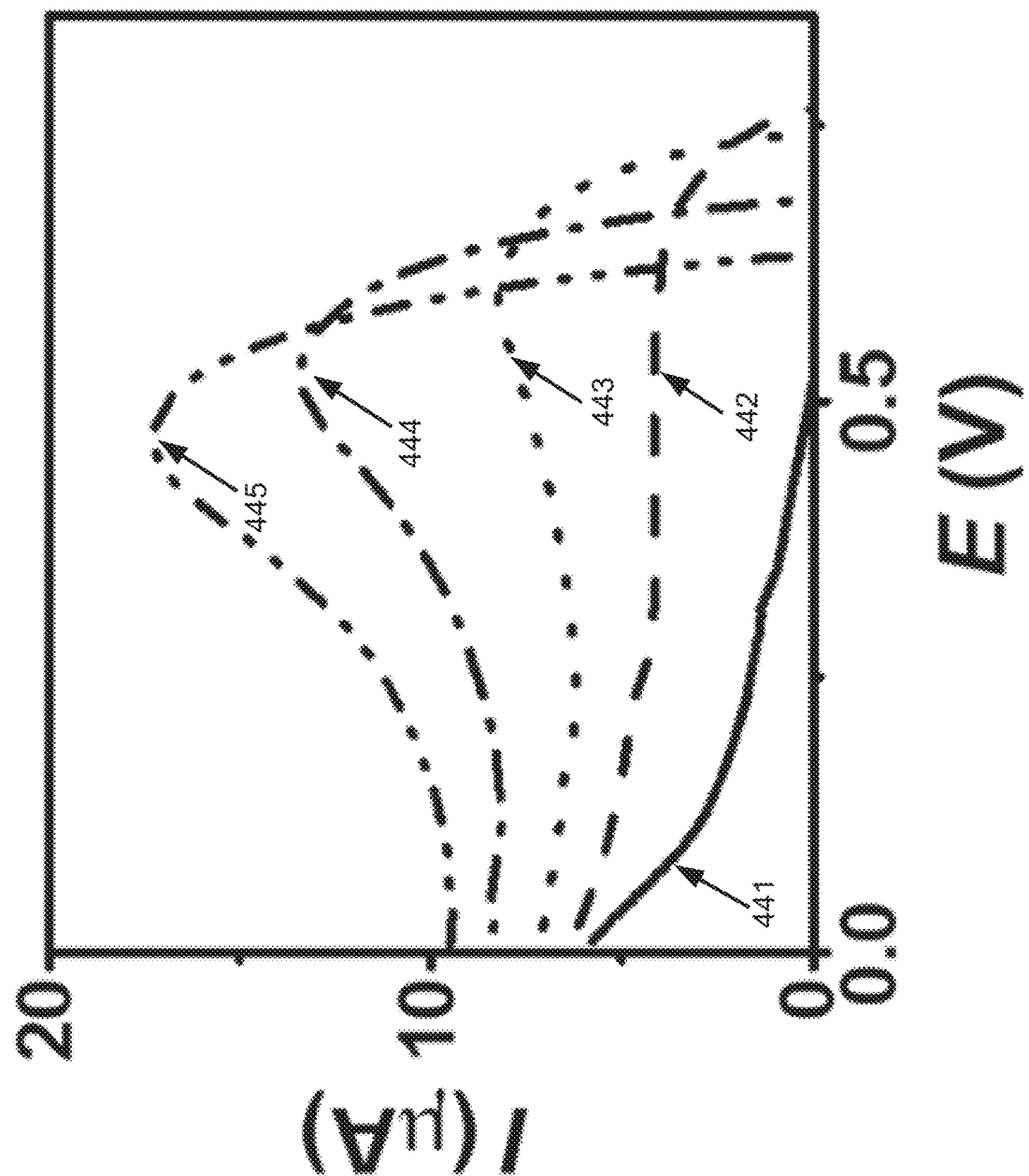
FIG. 4C shows polarization plots for an example embodiment of an implantable biofuel cell device in accordance with the disclosed technology.

FIG. 4C shows a data plot depicting polarization plots for an example embodiment of the implantable biofuel cell device 100 in PBS at pH 7.0 corresponding to the concentrations of lactate of 0, 2.5, 5.0, 7.5, 10.0 mM (which correspond to data curves 441, 442, 443, 444, and 445, respectively).

Figure 4D:
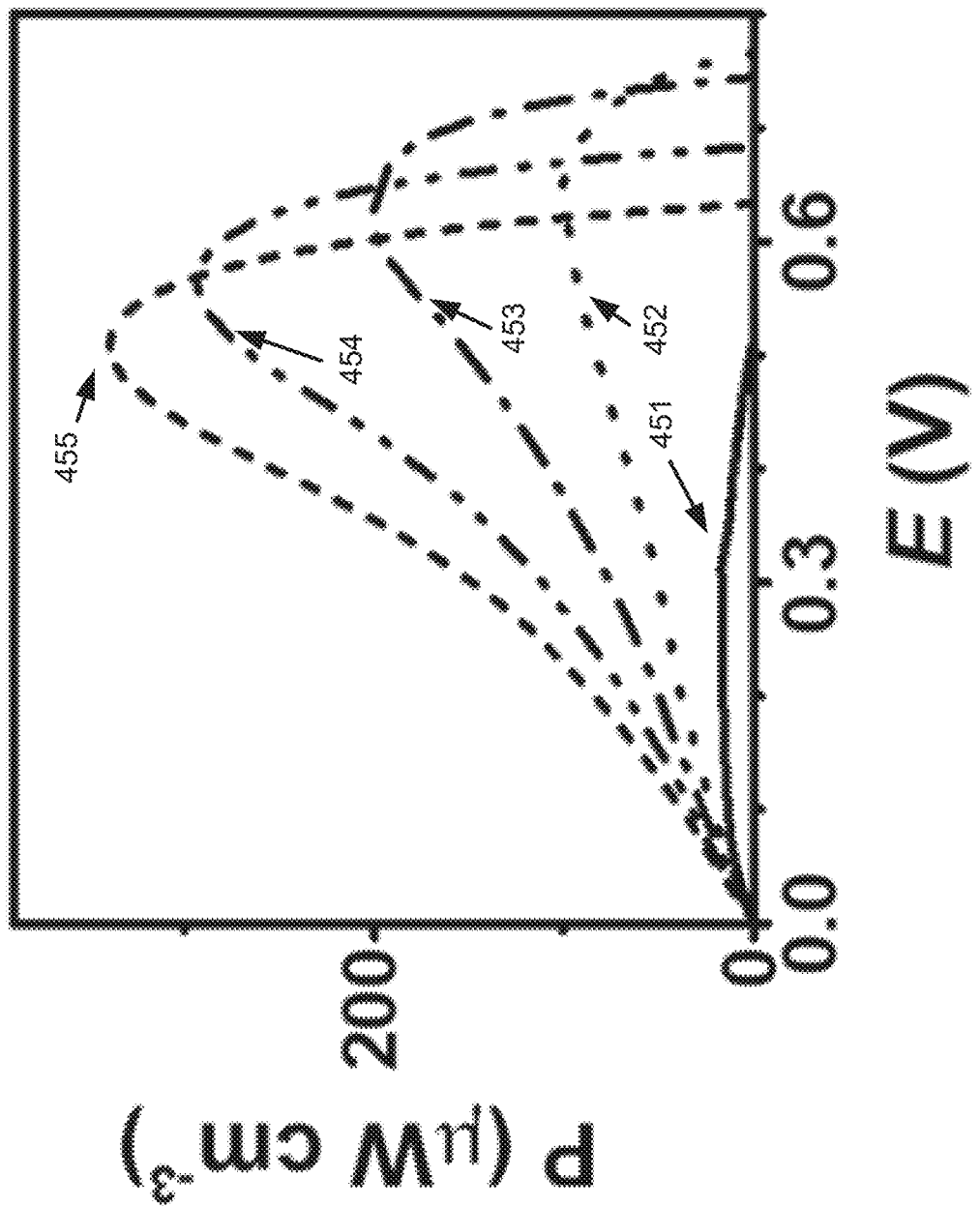
FIG. 4D shows power density versus voltage plots for an example embodiment of an implantable biofuel cell device in accordance with the disclosed technology.

FIG. 4D shows a data plot depicting power density versus voltage plots for an embodiment of the implantable biofuel cell device 100 in PBS at pH 7.0 corresponding to the concentrations of lactate of 0, 2.5, 5.0, 7.5, 10.0 mM (curves 451, 452, 453, 454, and 455, respectively).

In the example implementations, to examine the capacitance of the example biofuel cell device, cyclic voltammograms (CV) were performed at different scan rates. As the scan rate was increased, the current reading increased proportionally as well.

Figure 4E:
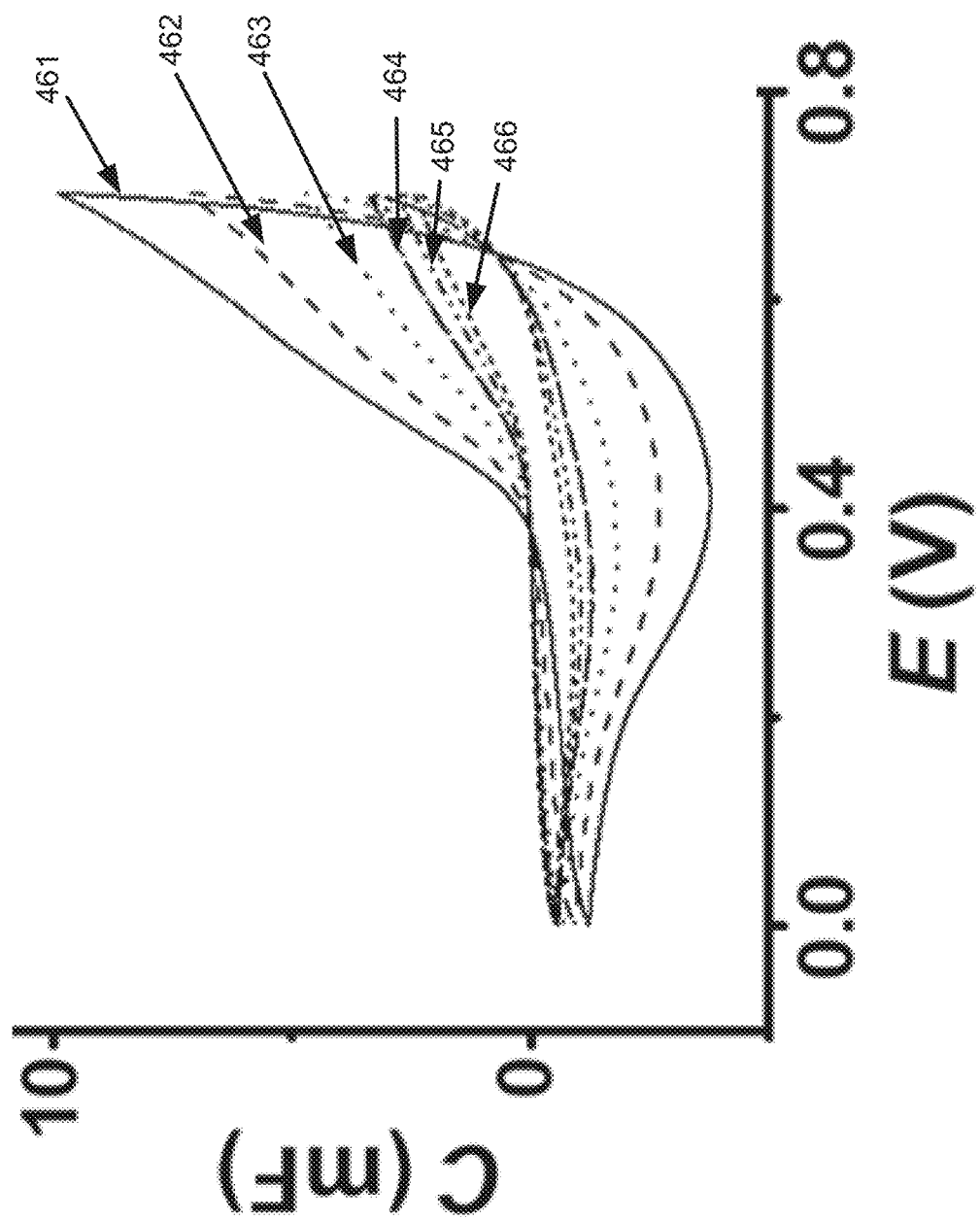
FIG. 4E shows apparent capacitance profiles at different scan rates for an example embodiment of an implantable biofuel cell device in accordance with the disclosed technology.

FIG. 4E shows apparent capacitance profiles at different scan rates for an example embodiment of the implantable biofuel cell device 100. Profiles 461, 462, 463, 464, 465, and 466 correspond to the scan rates of 10, 25, 50, 75, and 100 (mV s$^{-1}$), respectively. Drops at specific capacitances were observed at a faster scan rate. The voltammograms showed that a high capacitance in the example biofuel cell device can be achieved at a proper charge propagation within the potential window of 0 to ~0.6 V.

Figure 4F:
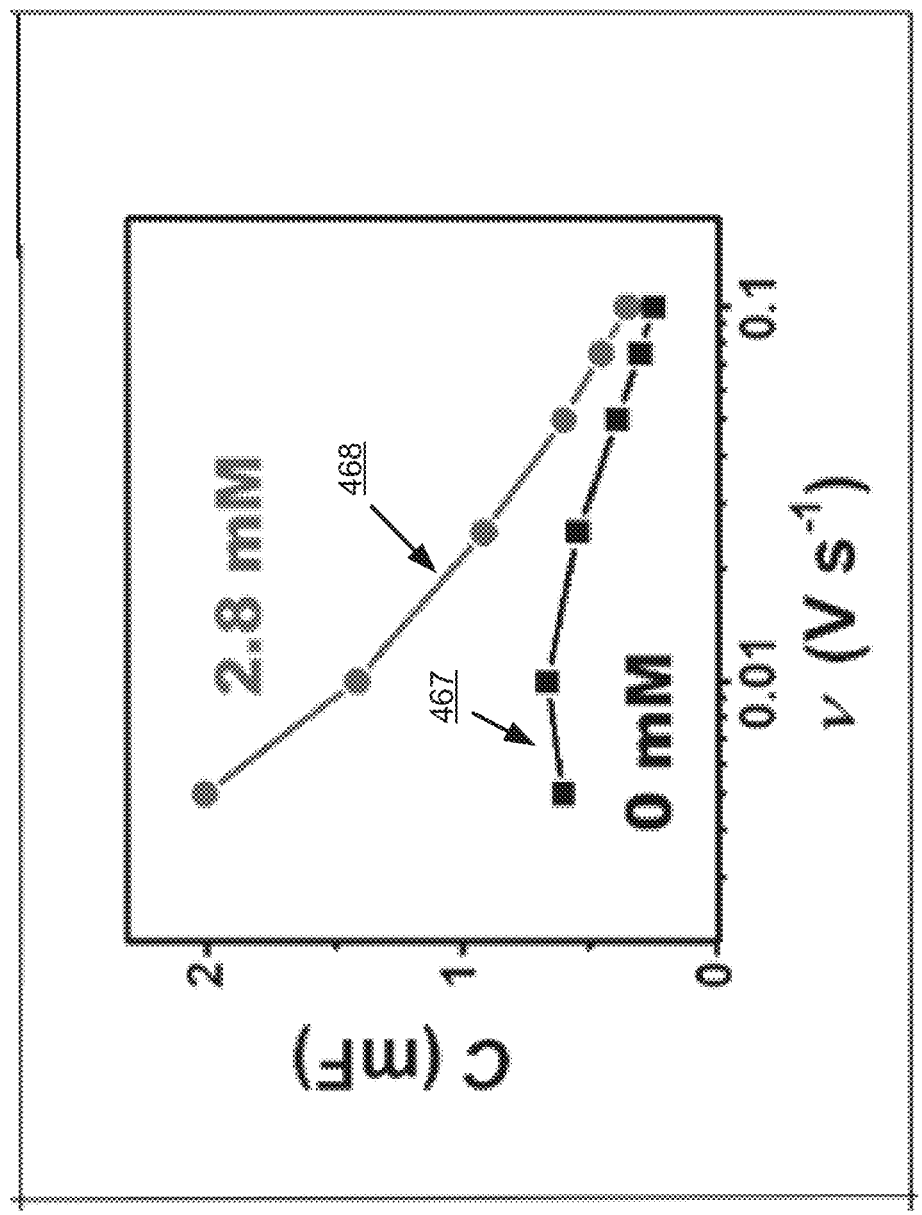
FIG. 4F shows the apparent capacitance versus scan rate for different concentrations of the fuel source for an example embodiment of an implantable biofuel cell device in accordance with the disclosed technology.

FIG. 4F shows the apparent capacitance versus scan rate for different concentrations of the lactate for an example embodiment of the implantable biofuel cell device 100. Curves 467 and 468 correspond to the concentrations of lactate 0 mM and 2.8 mM, respectively.

Figure 4G:
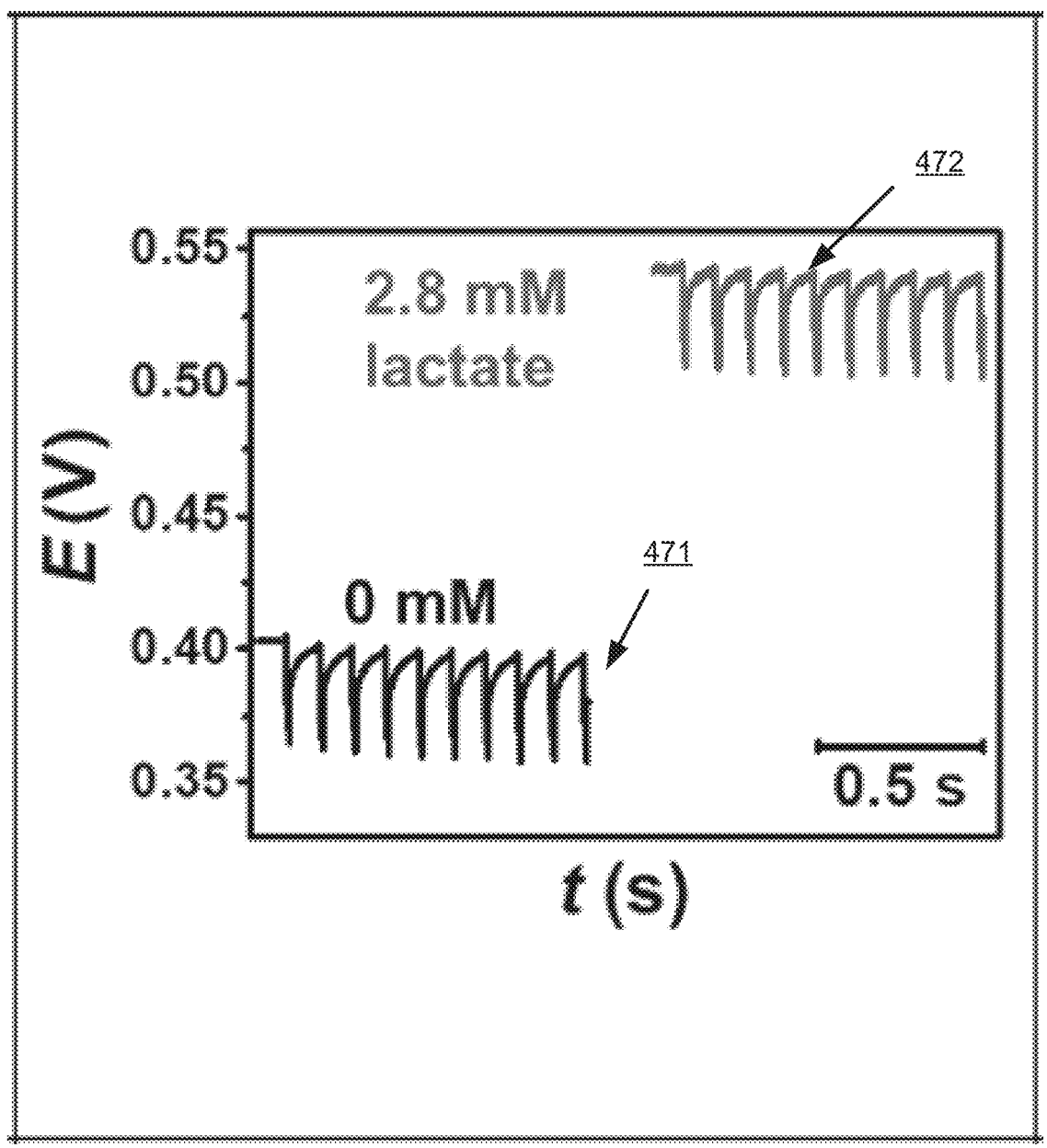
FIG. 4G shows voltage recordings while harvesting current pulses in the absence and presence of 2.8 mM lactate in an artificial CSF for an example embodiment of an implantable biofuel cell device in accordance with the disclosed technology.

FIG. 4G shows voltage recordings while harvesting current pulses in the absence (471) and presence (472) of 2.8 mM lactate in the artificial CSF. Current pulses had 10 Hz repetition rate, 100-μA amplitude, and 0.2 ms pulse width.

Figure 4H:
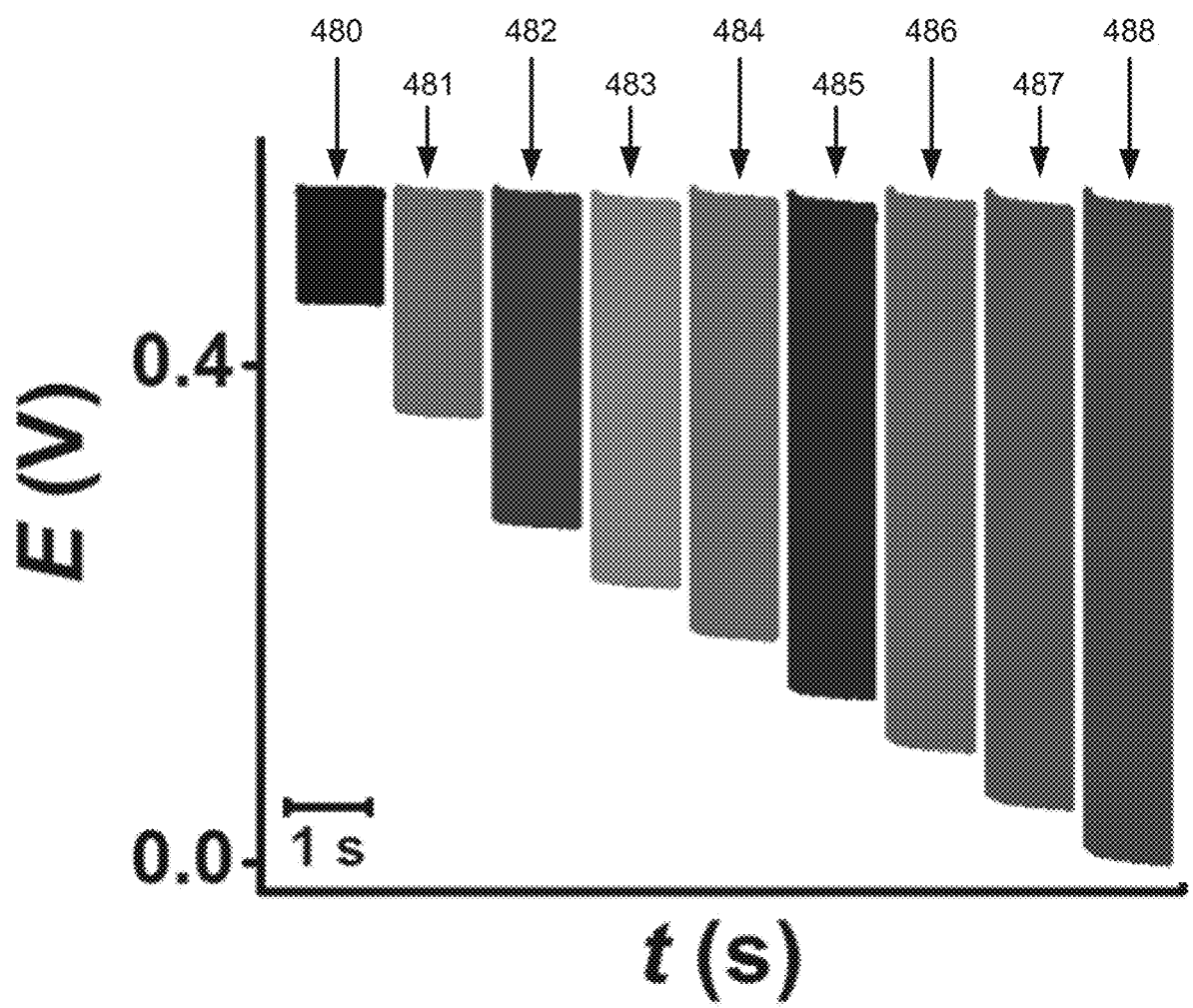
FIG. 4H shows voltage recordings while harvesting different current pulses in the presence of 2.8 mM lactate in the artificial CSF for an example embodiment of an implantable biofuel cell device in accordance with the disclosed technology.

FIG. 4H shows voltage recordings while harvesting current pulses of different amplitudes in the presence of 2.8 mM lactate in the artificial CSF. Traces 480, 481, 482, 483, 484, 485, 486, 487, and 488 correspond to the current pulses amplitudes of 0.50, 1.00, 1.50, 1.75, 2.00, 2.25, 2.50, 2.75, and 3.00 mA, respectively. Pulse repetition rate was 40 Hz, and pulse width was 0.2 ms.

The voltage and current pulse profiles shown in FIG. 1E illustrate that capacitive ($\Delta V_{capacitive}$) and resistive ($\Delta V_{ohmic}$) contributions cause a decrease in the open circuit voltage OCV (also referred to as $V_{max}$). For example, $\Delta V_{capacitive}$ and $\Delta V_{ohmic}$ can be seen in FIG. 1. For the example embodiment of the biofuel cell device used in the example implementations, the voltage loss due to resistive behaviors represented an equivalent series resistance (ESR) below 200Ω. The values of capacitance C, estimated by analyzing the voltage slope, were in the range of 10-500 μF cm$^{-3}$, e.g., reflecting the charge-storing performance of the example biofuel cell device. Through the analysis of the example biofuel cell device behavior at different currents (FIG. 4H), a power curve for the example biofuel cell device was generated. The power curve could display a maximum power output above 15 μW cm$^{-3}$ at a current of 60 mA cm$^{-3}$ and an OCV above 0.4 mV. The BFC self-charging behavior was examined using charge/discharge cycling at 40 Hz. After each discharge pulse, the example biofuel cell device recovered itself to its starting OCV as a result of the continuous enzymatic and catalytic reactions of lactate and oxygen at the anode and cathode electrodes of the BFC device, respectively. Larger voltage drops occurred when higher currents were applied, resulting in a longer recovery time back to the initial OCV.

Figure 4I:
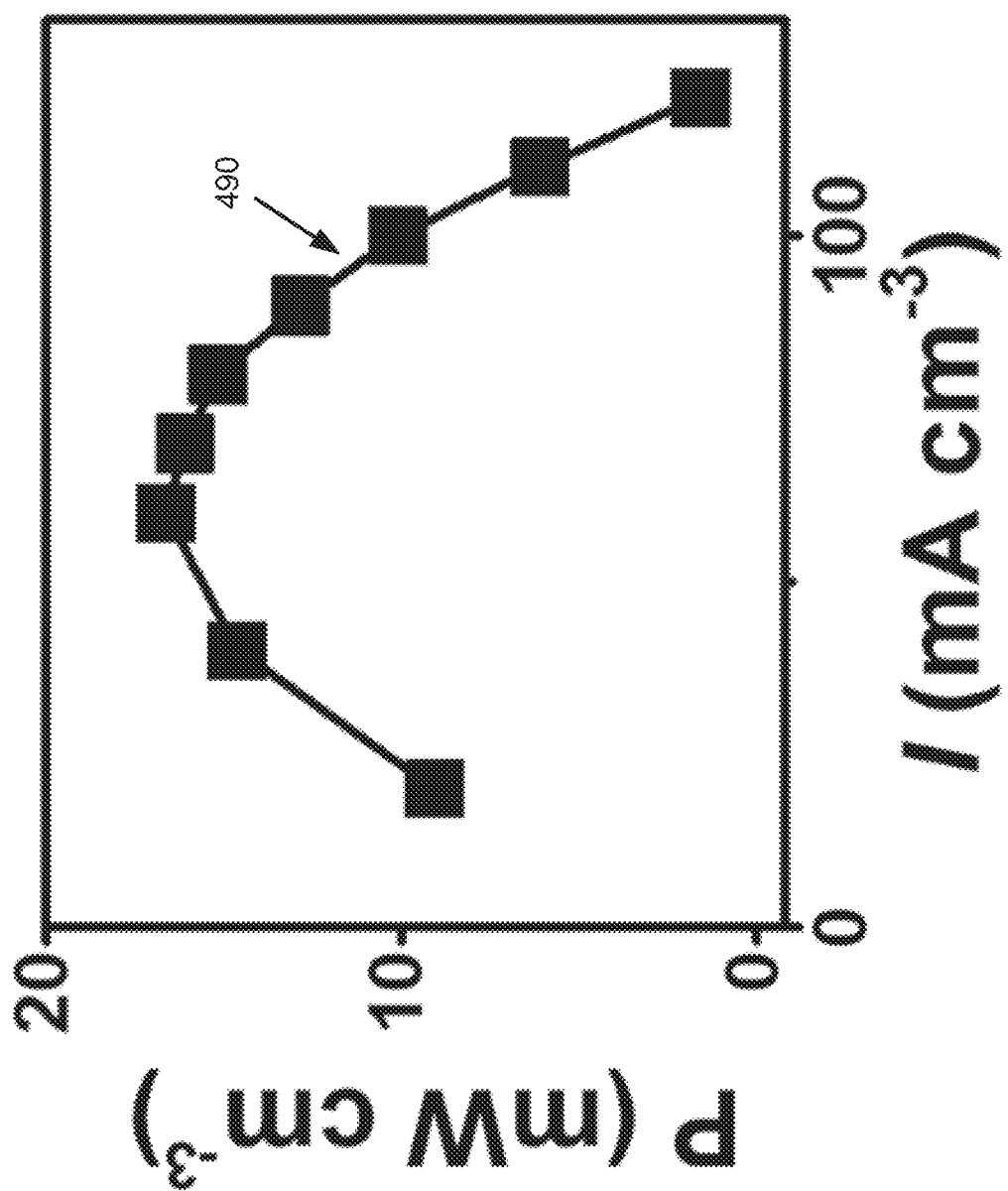
FIG. 4I shows a power curve profile for an example embodiment of an implantable biofuel cell device in accordance with the disclosed technology.

FIG. 4I shows a power curve profile 490 for an example embodiment of an implantable biofuel cell device 100. The power curve profile was calculated from the minimum voltage, which can be defined as OCV−$\Delta V_{capacitive}$−$\Delta V_{ohmic}$ (e.g., as illustrated in FIG. 1F). The highest value of the minimum power density ($P_{min}$) could reach above 15 mW cm$^{-3}$ was then obtained. A voltage drop, whose intensity is observed after a current pulse is applied, depends on the applied current. After a 0.2 ms pulse, the potential quickly resets to its initial value.

Figure 5:
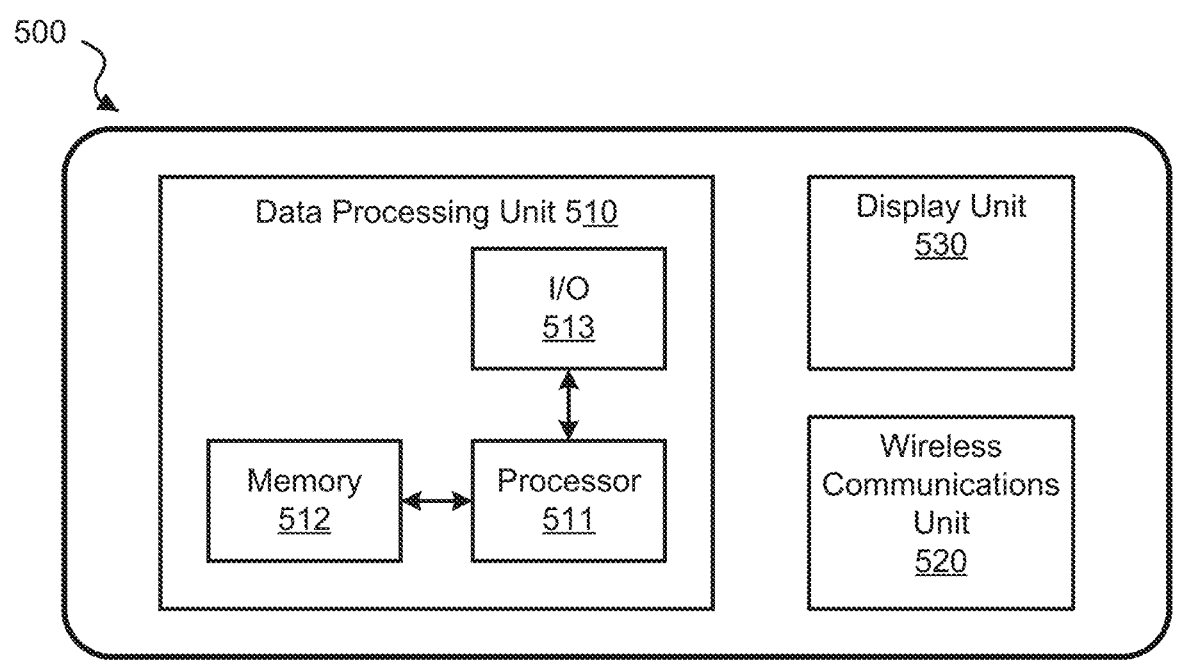
FIG. 5 shows a block diagram of an example embodiment of an electronic device that can interface with various embodiments of the biofuel cell device and/or integrated medical device for various implementations.

FIG. 5 shows a block diagram of an example embodiment of an electronic device 500 that can interface with various embodiments of the biofuel cell device 100 and/or integrated medical device for various implementations. For example, the electronic device 500 can connect an electrical circuit of the electronic device 500 with the elements 160 and 161 of the device 100; whereas in some embodiments, the electronic device 500 is coupled to an electronic interface of the medical device contingent of the integrated medical device/biofuel cell device. In various implementations, the electronic device 500 operable to store and execute the software application and algorithms and implement various controls of the biofuel cell device 100 and/or functionalities of a medical device integrated with the biofuel cell device 100. In various implementations, the electronic device 500 can be implemented as a portable computing device, such as a mobile communications device, such as a smartphone, tablet or wearable device, like a smartwatch, glasses, etc.; and/or the electronic device 500 can be implemented as a stationary computing device, such as a desktop computer. In some embodiments, the electronic device 500 includes a dongle that couples to the elements 160 and 161 of the device 100 and/or the medical device contingent to wirelessly connect to the computing components (e.g., a data processing unit) of the electronic device 500.

In some embodiments, the electronic device 500 includes a data processing unit 510 includes a processor 511 to process data, a memory 512 in communication with the processor 511 to store data, and an input/output unit (I/O)

513 to interface the processor 511 and/or memory 512 to other modules, units or devices, including other external computing devices. For example, the processor 511 can include a central processing unit (CPU) or a microcontroller unit (MCU). For example, the memory 512 can include and store processor-executable code, which when executed by the processor, configures the data processing unit 510 to perform various operations, e.g., such as receiving information, commands, and/or data, processing information and data, and transmitting or providing information/data to another device. In some implementations, the data processing unit 510 can transmit raw or processed data to a computer system or communication network accessible via the Internet (referred to as 'the cloud') that includes one or more remote computational processing devices (e.g., servers in the cloud). To support various functions of the data processing unit 510, the memory 512 can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory 512. In some embodiments, the data processing unit 510 includes a wireless communication unit 520, such as a wireless transmitter to transmit stored and/or processed data or a wireless transceiver (Tx/Rx) to transmit and receive data. The I/O 513 of the data processing unit 510 can interface the data processing unit 510 with the wireless communications unit 520 to utilize various types of wired or wireless interfaces compatible with typical data communication standards, for example, which can be used in communications of the data processing unit 510 with other devices, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), and parallel interfaces. In some embodiments, the data processing unit 510 includes a display unit 530, which can include a visual display such as a display screen, an audio display such as a speaker, or other type of display or combinations thereof. The I/O 513 of the data processing unit 510 can also interface with other external interfaces, sources of data storage, and/or visual or audio display devices, etc. to retrieve and transfer data and information that can be processed by the processor 511, stored in the memory 512, or exhibited on an output unit (e.g., display unit 530) of the electronic device 500 or an external device. For example, the display unit 530 can be configured to be in data communication with the data processing unit 510, e.g., via the I/O 513, to provide a visual display, an audio display, and/or other sensory display that produces the user interface of the software application. In some examples, the display unit 530 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In some example implementations, various example embodiments of the biofuel cell device 100 can be electrically interfaced to a medical device that includes the electronic device 500, such that the biofuel cell device 100 harvests electrical energy from a biological fluid where the biofuel cell device 100 is implanted (e.g., converting bio/chemical energy into electrical energy), and the generated electrical energy will be managed by the electronic device 500 of the integrated medical device for various actuatable functions of the medical device. In examples where the medical device includes a catheter for electrical stimulation, the biofuel cell device 100 supplies the electrical energy used to actuate electrical stimulation output by the catheter to the target location for the stimulation application. In some implementations of the integrated biofuel cell device 100 integrated with a medical device as an implantable spinal cord catheter device, for example, the electronic device 500 can control the catheter functionality, such as direct current in the dorsal column or dorsal horn of the spinal cord to cause increased gamma-aminobutyric acid (GABA) neurotransmitter, e.g., resulting in decreased peripheral-to-central pain transmission. In some example implementations, the medical device can include sensors (e.g., biosensors), where the harvested electrical energy can be used by the self-charging medical device for sensing applications.

EXAMPLES

In some embodiments in accordance with the disclosed technology (example A1), a biofuel cell device for extracting energy from a biological fluid includes a substrate that includes a first compartment having a first hollow interior portion and a second compartment having a second hollow interior portion, wherein the first hollow interior portion of the first compartment and the second hollow interior portion of the second compartment are separated, the substrate including one or more openings into each of the first hollow interior portion and the second hollow interior portion; an anode assembly that includes an anode electrode disposed in the first hollow interior portion of the substrate and a functionalization material disposed on or integrated with the anode electrode proximate the one or more openings, in which the functionalization material includes a catalyst molecule to facilitate conversion of a substance in a biological fluid to a first product in an oxidative process that releases electrons captured at the anode electrode, thereby extracting energy from the substance in the biological fluid; and a cathode assembly that includes a cathode electrode disposed in the second hollow interior portion of the substrate separated from the anode electrode, the cathode assembly including a catalytic material operable to reduce an oxygenated substance in the biological fluid to a second product in a chemical reduction process in which the second product gains electrons.

Example A2 includes the biofuel cell device as in example A1, in which the anode assembly includes a surface having a plurality of cavities in which the functionalization layer is disposed over the anode electrode.

Example A3 includes the biofuel cell device as in examples A1 or A2, further including a cover disposed over the anode assembly, the cover having a plurality of openings that expose at least some portions of the anode contingent.

Example A4 includes the biofuel cell device as in example A3, in which the cover is a polymer tubing that tightly surrounds the anode assembly.

Example A5 includes the biofuel cell device as in example A3, in which the cover includes a biocompatible material.

Example A6 includes the biofuel cell device as in example A5, in which the biocompatible material includes polydimethylsiloxane (PDMS), polytetrafluoroethylene (PTFE), or polyurethane (PU).

Example A7 includes the biofuel cell device as in any of the preceding examples, in which the functionalization layer includes a mediator layer disposed on the anode electrode and an enzymatic layer disposed on the mediator layer.

Example A8 includes the biofuel cell device as in any of the preceding examples, in which the device is operable to provide the extracted energy to an implantable medical device.

Example A9 includes the biofuel cell device as in any of the preceding examples, in which the device is operable to provide the extracted energy as a pulse generator for treating refractory chronic pain through stimulation in a spinal cord of a patient.

Example A10 includes the biofuel cell device as in any of the preceding examples, in which the substance in the biological fluid includes glucose, the catalyst includes glucose oxidase (GOx), and the first product includes gluconolactone, or in which the substance in the biological fluid includes lactate, the catalyst includes lactate oxidase (LOx), and the first product includes pyruvate.

Example A11 includes the biofuel cell device as in any of the preceding examples, in which the catalytic material includes platinum.

Example A12 includes the biofuel cell device as in any of the preceding examples, further including an amplifier circuit to supply electrical current from the extracted energy to another device that electrically couples to the biofuel cell device.

Example A13 includes the biofuel cell device as in example A12, in which the enzymatic biofuel cell and the amplifier circuit are coupled to a single substrate.

In some embodiments in accordance with the disclosed technology (example B1), an implantable biofuel cell device for extracting energy from a biological fluid includes a substrate, including (i) a first compartment having a first hollow interior portion and (ii) a second compartment having a second hollow interior portion, the second hollow interior portion separated from the first hollow interior portion, wherein the substrate includes one or more openings into each of the first hollow interior portion and the second hollow interior portion; an anode assembly, including (i) a first electrode disposed in the first hollow interior portion of the substrate and (ii) a functionalization material disposed on or integrated with the first electrode proximate the one or more openings, wherein the functionalization material includes a catalyst to facilitate conversion of a substance in the biological fluid to a first product in an oxidative process that releases electrons captured at the first electrode; and a cathode assembly, including (i) a second electrode disposed in the second hollow interior portion of the substrate and (ii) a catalytic material to reduce an oxygenated substance in the biological fluid to a second product in a chemical reduction process in which the second product gains electrons, wherein, when the biofuel cell device is inserted in a tissue exposing the biofuel cell device to the biological fluid, the biofuel cell device is operable to extract electrical energy from the substance in the biological fluid across the anode assembly and the cathode assembly.

Example B2 includes the biofuel cell device as in any of examples B1-B17, wherein the first compartment of the substrate includes a first elongated tube includes a surface having a plurality of the openings on at least a portion of a longitudinal side that spans the length of the first elongated tube, and wherein the second compartment of the substrate includes a second elongated tube includes a surface having a plurality of the openings on at least a portion of a longitudinal side that spans the length of the second elongated tube.

Example B3 includes the biofuel cell device as in any of examples B1-B17, further comprising a cover disposed over the substrate, the cover having a plurality of apertures that expose at least some portions of the anode assembly and of the cathode assembly.

Example B4 includes the biofuel cell device as in any of examples B1-B17, wherein the first elongated tube and the second elongated tube include a biocompatible polymer material.

Example B5 includes the biofuel cell device as in any of examples B1-B17, wherein the biocompatible polymer material includes one or more of polydimethylsiloxane (PDMS), polytetrafluoroethylene (PTFE), or polyurethane (PU).

Example B6 includes the biofuel cell device as in any of examples B1-B17, wherein the functionalization material of the anode assembly includes a conductive polymer material.

Example B7 includes the biofuel cell device as in any of examples B1-B17, wherein the functionalization material of the anode assembly includes multi-walled carbon nanotubes.

Example B8 includes the biofuel cell device as in any of examples B1-B17, wherein the functionalization material of the anode assembly includes a redox mediator to increase electron conductivity within the functionalization material.

Example B9 includes the biofuel cell device as in any of examples B1-B17, wherein the redox mediator includes 1,4-naphthoquinone (NQ).

Example B10 includes the biofuel cell device as in any of examples B1-B17, wherein the catalytic material of the cathode assembly includes a conductive polymer material.

Example B11 includes the biofuel cell device as in any of examples B1-B17, wherein the catalytic material of the cathode assembly includes multi-walled carbon nanotubes.

Example B12 includes the biofuel cell device as in any of examples B1-B17, wherein the catalytic material of the cathode assembly includes polychlorotrifluoroethylene (PCTFE) to mitigate effects of oxygen fluctuations in the biological fluid during an operation of the biofuel cell device.

Example B13 includes the biofuel cell device as in any of examples B1-B17, wherein the one or both of the first electrode and second electrode includes platinum.

Example B14 includes the biofuel cell device as in any of examples B1-B17, wherein the biofuel cell device is integrated with an implantable medical device to provide the extracted electrical energy to the implantable medical device.

Example B15 includes the biofuel cell device as in any of examples B1-B17, wherein the implantable medical device and the biofuel cell device are integrated as a spinal catheter, and wherein the biofuel cell device is operable to provide the extracted electrical energy to the spinal catheter to enable the spinal catheter to generate electrical pulses.

Example B16 includes the biofuel cell device as in any of examples B1-B17, further comprising an electrical circuit to supply electrical current from the extracted electrical energy to an external device that electrically couples to the biofuel cell device.

Example B17 includes the biofuel cell device as in any of examples B1-B16, wherein the substance in the biological fluid includes glucose, the catalyst includes glucose oxidase (GOx), and the first product includes gluconolactone, and/or wherein the substance in the biological fluid includes lactate, the catalyst includes lactate oxidase (LOx), and the first product includes pyruvate.

In some embodiments in accordance with the disclosed technology (example B18), a self-charging medical device includes a catheter comprising a first elongated tube and a second elongated tube coupled to the first elongated tube at one or more coupling positions along a longitudinal side of the first and second elongated tubes, the first elongated tube including a first compartment having a first hollow interior portion and a plurality of openings from an outer surface of the first elongated tube into the first hollow interior portion, the second elongated tube including a second compartment having a second hollow interior portion and a plurality of openings from an outer surface of the second elongated tube into the second hollow interior portion, wherein the second hollow interior portion is separated from the first hollow interior portion, and wherein the first and second elongated tubes include a bendable material; and a biofuel cell integrated in the catheter and comprising an anode assembly disposed in the first elongated tube and a cathode assembly disposed in the second elongated tube, the biofuel cell operable to extract electrical energy from a substance in a biological fluid across the anode assembly and the cathode assembly to supply the extracted electrical energy for the catheter. The anode assembly includes a first wire and a first substance, the first wire and the first substance disposed within the first hollow interior portion, wherein the first substance is coupled to at least a portion of the first wire proximate the plurality of openings of the first elongated tube, and wherein the first substance includes a functionalization material comprising a catalyst to facilitate conversion of the substance in the biological fluid to a first product in an oxidative process that releases electrons captured at the first wire. The cathode assembly includes a second wire and a second substance, the second wire and the second substance disposed within the second hollow interior portion, wherein the second substance is coupled to at least a portion of the second wire proximate the plurality of openings of the second elongated tube, and wherein the second substance includes a catalytic material to reduce an oxygenated substance in the biological fluid to a second product in a chemical reduction process in which the second product gains electrons.

Example B19 includes the medical device as in any of examples B18-B28, wherein the catheter is configured as a spinal catheter, such that the biofuel cell is operable to provide the extracted electrical energy to the spinal catheter to enable actuation of the spinal catheter to generate electrical pulses.

Example B20 includes the medical device as in any of examples B18-B28, further comprising a cover disposed over the at least a portion of the first elongated tube and the second elongated tube, the cover having a plurality of apertures that expose at least some portions of the anode assembly and of the cathode assembly through the plurality of openings of the first hollow interior portion and the second hollow interior portion, respectively.

Example B21 includes the medical device as in any of examples B18-B28, wherein the bendable material of the first elongated tube and the second elongated tube include a biocompatible polymer material comprising one or more of polydimethylsiloxane (PDMS), polytetrafluoroethylene (PTFE), or polyurethane (PU).

Example B22 includes the medical device as in any of examples B18-B28, wherein the functionalization material of the anode assembly includes one or both of a conductive polymer material and multi-walled carbon nanotubes.

Example B23 includes the medical device as in any of examples B18-B28, wherein the functionalization material of the anode assembly includes a redox mediator including 1,4-naphthoquinone (NQ) to increase electron conductivity within the functionalization material.

Example B24 includes the medical device as in any of examples B18-B28, wherein the second substance of the cathode assembly includes one or both of a conductive polymer material and multi-walled carbon nanotubes.

Example B25 includes the medical device as in any of examples B18-B28, wherein the catalytic material of the cathode assembly includes polychlorotrifluoroethylene (PCTFE) to mitigate effects of oxygen fluctuations in the biological fluid during an operation of the biofuel cell device.

Example B26 includes the medical device as in any of examples B18-B28, wherein the one or both of the first wire and second wire includes platinum.

Example B27 includes the medical device as in any of examples B18-B28, further comprising an electrical circuit coupled to the biofuel cell and operable to supply electrical current from the extracted electrical energy to an external device that electrically couples to the biofuel cell device.

Example B28 includes the medical device as in any of examples B18-B27, wherein the substance in the biological fluid includes glucose, the catalyst includes glucose oxidase (GOx), and the first product includes gluconolactone, and/or wherein the substance in the biological fluid includes lactate, the catalyst includes lactate oxidase (LOx), and the first product includes pyruvate.

In some embodiments in accordance with the disclosed technology (example B29), a biofuel cell device for extracting energy from a biological fluid includes an anode assembly comprising: a first hollow elongated element, a first substance at least partially disposed inside the first hollow elongated element and that is at least partially electrically conductive, a first electrically conductive elongated element at least partially disposed inside the first hollow elongated element and coupled with the first substance, wherein the first hollow elongated element has at least one opening in its surface to expose at least a portion of the first substance; and a cathode assembly comprising: a second hollow elongated element, at second substance at least partially disposed inside the second hollow elongated element and that is at least partially electrically conductive, a second electrically conductive elongated element at least partially disposed inside the second hollow elongated element and coupled with the second substance, wherein the second hollow elongated element has at least one opening in its surface to expose at least a portion of the second substance, wherein the biofuel cell device to is operable to facilitate conversion of a substance in the biological fluid to a first product in an oxidative process that releases electrons captured at the first electrically conductive elongated element of the anode assembly and to reduce an oxygenated substance in the biological fluid to a second product in a chemical reduction process in which the second product gains electrons, thereby extracting energy from the substance in the biological fluid across the anode and the cathode assemblies.

Example B30 includes the fuel cell device as in any of examples B29-B34, wherein the first substance comprises an enzyme.

Example B31 includes the fuel cell device as in any of examples B29-B34, wherein the second substance comprises a chemical compound which can catalyze a reduction reaction.

Example B32 includes the fuel cell device as in any of examples B29-B34, wherein the first substance comprises a chemical compound which is a redox mediator.

Example B33 includes the fuel cell device as in any of examples B29-B34, wherein the second substance comprises a compound capable to absorb oxygen.

Example B34 includes the fuel cell device as in any of examples B29-B33, wherein the second substance comprises a compound capable to adsorb oxygen.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. An implantable biofuel cell device for extracting energy from a biological fluid, comprising:
   a substrate, including (i) a first compartment including a first elongated tube with a surface having a first array of three or more openings on at least a portion of a longitudinal side that spans the length of the first elongated tube, the first elongated tube having a first hollow interior portion, and (ii) a second compartment including a second elongated tube with a surface having a second array of three or more openings on at least a portion of a longitudinal side that spans the length of the second elongated tube, the second elongated tube having a second hollow interior portion, wherein the first and second elongated tubes are configured to separate the second hollow interior portion from the first hollow interior portion;

an anode assembly, including (i) a anode electrode disposed in the first hollow interior portion of the substrate and (ii) a functionalization material disposed on or integrated with the anode electrode proximate the first array of three or more openings, wherein the functionalization material includes a catalyst to facilitate conversion of a substance in the biological fluid to a first product in an oxidative process that releases electrons captured at the anode electrode; and a cathode assembly, including (i) a cathode electrode disposed in the second hollow interior portion of the substrate and (ii) a catalytic material proximate the second array of three or more openings to reduce an oxygenated substance in the biological fluid to a second product in a chemical reduction process in which the second product gains electrons, wherein, when the biofuel cell device is inserted in a tissue exposing the biofuel cell device to the biological fluid, the biofuel cell device is operable to extract electrical energy from the substance in the biological fluid across the anode assembly and the cathode assembly.

2. The biofuel cell device as in claim 1, further comprising a cover disposed over the substrate, the cover having a plurality of apertures that expose at least some portions of the anode assembly and of the cathode assembly.

3. The biofuel cell device as in claim 1, wherein the first elongated tube and the second elongated tube include a biocompatible polymer material.

4. The biofuel cell device as in claim 3, wherein the biocompatible polymer material includes one or more of polydimethylsiloxane (PDMS), polytetrafluoroethylene (PTFE), or polyurethane (PU).

5. The biofuel cell device as in claim 1,
wherein the functionalization material of the anode assembly includes a conductive polymer material, or
wherein the catalytic material of the cathode assembly includes a conductive polymer material, or
wherein the functionalization material of the anode assembly includes a conductive polymer material and the catalytic material of the cathode assembly includes a conductive polymer material.

6. The biofuel cell device as in claim 5, wherein the conductive polymer material is in a form of a wire, a strip, a mesh, or a fiber.

7. The biofuel cell device as in claim 1, wherein the functionalization material of the anode assembly includes multi-walled carbon nanotubes.

8. The biofuel cell device as in claim 1, wherein the functionalization material of the anode assembly includes a redox mediator to increase electron conductivity within the functionalization material.

9. The biofuel cell device as in claim 8, wherein the redox mediator includes 1,4-naphthoquinone (NQ).

10. The biofuel cell device as in claim 1, wherein the catalytic material of the cathode assembly includes multi-walled carbon nanotubes.

11. The biofuel cell device as in claim 1, wherein the catalytic material of the cathode assembly includes polychlorotrifluoroethylene (PCTFE) to mitigate effects of oxygen fluctuations in the biological fluid during an operation of the biofuel cell device.

12. The biofuel cell device as in claim 1, wherein the biofuel cell device is integrated with an implantable medical device to provide the extracted electrical energy to the implantable medical device.

13. The biofuel cell device as in claim 12, wherein the implantable medical device and the biofuel cell device are integrated as a spinal catheter, and wherein the biofuel cell device is operable to provide the extracted electrical energy to the spinal catheter to enable the spinal catheter to generate electrical pulses.

14. The biofuel cell device as in claim 1, further comprising an electrical circuit to supply electrical current from the extracted electrical energy to an external device that electrically couples to the biofuel cell device.

15. The biofuel cell device as in claim 1,
wherein the substance in the biological fluid includes glucose, the catalyst includes glucose oxidase (GOx), and the first product includes gluconolactone, and/or
wherein the substance in the biological fluid includes lactate, the catalyst includes lactate oxidase (LOx), and the first product includes pyruvate.

16. The biofuel cell device as in claim 1, wherein one or both of the first elongated tube and the second elongated tube has a ratio of its length to its width which is at least 1.1.

17. The biofuel cell device as in claim 1, wherein the first elongated tube and the second elongated tube are configured to separate the anode assembly and the cathode assembly by at least 5 µm.

18. The biofuel cell device as in claim 1, wherein the anode assembly includes a surface having a plurality of cavities in which the functionalization layer is disposed over the anode electrode.

19. The biofuel cell device as in claim 1, wherein the substrate includes a separation between the first hollow interior portion of the first elongated tube and the second hollow interior portion of the second elongated tube, wherein the separation includes (i) a wall structure that is part of one or both of the first elongated tube and the second elongated tube or (ii) a separate structure that connects at least a portion of the first elongated tube and the second elongated tube.

20. The biofuel cell device as in claim 1, wherein one or both of the first elongated tube and the second elongated tube have a diameter up to 900 µm.

21. The biofuel cell device as in claim 1, wherein the three or more openings of one or both of the first array and the second array include circular openings.

* * * * *